(12) United States Patent
Kennedy et al.

(10) Patent No.: US 11,014,047 B2
(45) Date of Patent: May 25, 2021

(54) MICROFABRICATION OF A MICRODIALYSIS PROBE WITH NANOPOROUS MEMBRANE

(71) Applicant: THE REGENTS OF THE UNIVERSITY OF MICHIGAN, Ann Arbor, MI (US)

(72) Inventors: Robert T. Kennedy, Ann Arbor, MI (US); Hyeun Joong Yoon, Brookings, SD (US); Thitaphat Ngernsutivorakul, Ann Arbor, MI (US); Woong Hee Lee, Goleta, CA (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 221 days.

(21) Appl. No.: 15/764,124

(22) PCT Filed: Nov. 29, 2016

(86) PCT No.: PCT/US2016/063930
§ 371 (c)(1),
(2) Date: Mar. 28, 2018

(87) PCT Pub. No.: WO2017/100028
PCT Pub. Date: Jun. 15, 2017

(65) Prior Publication Data
US 2018/0272287 A1    Sep. 27, 2018

Related U.S. Application Data
(60) Provisional application No. 62/264,465, filed on Dec. 8, 2015.

(51) Int. Cl.
*B01D 61/24* (2006.01)
*B01D 67/00* (2006.01)
(Continued)

(52) U.S. Cl.
CPC ............ *B01D 61/243* (2013.01); *A61B 5/145* (2013.01); *A61B 5/14525* (2013.01);
(Continued)

(58) Field of Classification Search
CPC ............ B01D 67/0062; B01D 67/0065; B01D 71/02; B01D 71/025; B01D 61/025;
(Continued)

(56) References Cited

U.S. PATENT DOCUMENTS
5,462,645 A    10/1995   Albery et al.
8,535,537 B2    9/2013   Feichtner et al.
(Continued)

FOREIGN PATENT DOCUMENTS
JP      2010504787 A    2/2010
WO    WO-2014053840 A1    4/2014

OTHER PUBLICATIONS
International Search Report and Written Opinion of the International Searching Authority issued in PCT/US2016/063930, dated Mar. 15, 2017; ISA/KR.
(Continued)

*Primary Examiner* — John Kim
(74) *Attorney, Agent, or Firm* — Marshall, Gerstein & Borun LLP

(57) ABSTRACT

Microdialysis sampling is an essential tool for in vivo neuro-chemical monitoring. Conventional dialysis probes are over 220 μm in diameter and have limited flexibility in design because they are made by assembly using preformed membranes. The probe size constrains spatial resolution and governs the amount of tissue damaged caused by probe insertion. To overcome these limitations, we have developed a method to microfabricate probes in Si that are 45 μm thick 180 μm wide. The probes contain a buried, U-shaped chan-
(Continued)

nel that is 30 μm deep 60 μm wide and terminates in ports for external connection. A 4 mm length of the probe is covered with a 5 μm thick nanoporous membrane. The membrane was microfabricated by deep reactive ion etching through a porous aluminum oxide layer. The microfabricated probe has cross-sectional area that is 79% less than that of the smallest conventional microdialysis probes. The probes yield 2-7% relative recovery at 100 nL/min perfusion rate for a variety of small molecules. The probe was successfully tested in vivo by sampling from the striatum of live rats. Fractions were collected at 20 min intervals (2 μL) before and after an injection of 5 mg/kg, i.p amphetamine. Analysis of fractions by liquid chromatography-mass spectrometry revealed reliable detection of 13 neurochemicals, including dopamine and acetylcholine, at basal conditions. Amphetamine evoked a 43-fold rise in dopamine, a result nearly identical to a conventional dialysis probe in the same animal. The microfabricated probes have potential for sampling with higher spatial resolution and less tissue disruption than conventional probes. It may also be possible to add functionality to the probes by integrating other components, such as electrodes, optics, and additional channels.

27 Claims, 20 Drawing Sheets

(51) Int. Cl.
| | |
|---|---|
| B01D 71/02 | (2006.01) |
| G01N 1/10 | (2006.01) |
| G01N 33/487 | (2006.01) |
| A61B 5/145 | (2006.01) |
| C25D 11/04 | (2006.01) |
| C25D 11/10 | (2006.01) |
| C25D 11/24 | (2006.01) |
| B01D 61/02 | (2006.01) |

(52) U.S. Cl.
CPC ..... *B01D 67/0062* (2013.01); *B01D 67/0065* (2013.01); *B01D 71/02* (2013.01); *B01D 71/025* (2013.01); *C25D 11/045* (2013.01); *C25D 11/10* (2013.01); *C25D 11/24* (2013.01); *G01N 1/10* (2013.01); *G01N 33/487* (2013.01); *A61B 2562/12* (2013.01); *B01D 61/025* (2013.01)

(58) Field of Classification Search
CPC ... B01D 61/243; A61B 5/145; A61B 5/14525; A61B 2562/12; C25D 11/045; C25D 11/10; C25D 11/24; G01N 33/487
See application file for complete search history.

(56) References Cited

U.S. PATENT DOCUMENTS

| | | | | |
|---|---|---|---|---|
| 8,790,586 | B2* | 7/2014 | O'Connell | B01D 61/243 422/255 |
| 2001/0045122 | A1 | 11/2001 | Ehwald et al. | |
| 2014/0069861 | A1 | 3/2014 | Browning et al. | |

OTHER PUBLICATIONS

Ainla et al., A multifunctional pipette, Lab Chip 2012, 12, 1255-1261.
Benveniste et al., Microdialysis—theory and application, Prog. Neurobiol. 1990, 35, 195-215.
Boyd et al., Trace-level amino acid analysis by capillary liquid chromatography and application to in vivo microdialysis sampling with 10-s temporal resolution, Anal. Chem. 2000, 72, 865-871.
Bungay et al., Microdialysis of dopamine interpreted with quantitative model incorporating probe implantation trauma, J. Neurochem. 2003, 86, 932-946.
Butcher et al., Amphetamine-induced dopamine release in the rat striatum: an in vivo microdialysis study, J. Neurochem. 1988, 50, 346-355.
Chandrasekaran et al., Surface micromachined metallic microneedles, J. Microelectromech. Syst. 2003, 12, 281-288.
Chen et al., Dry-coated microprojection array patches for targeted delivery of immunotherapeutics to the skin, J. Control Release, 2009, 139, 212-220.
Chung et al., Highly permeable silicon membranes for shear free chemotaxis and rapid cell labeling, Lab Chip, 2014, 14, 2456-2468.
Church et al., Rapid sampling and determination of extracellular dopamine in vivo, Anal. Chem. 1987, 59, 712-716.
Darvesh et al., In vivo brain microdialysis: advances in neuropsychopharmacology and drug discovery, Exp. Opin. Drug Discov. 2011, 6, 109-127.
Desai et al., Characterization of micromachined silicon membranes for immunoisolation and bioseparation applications, J. Membr. Sci. 1999, 159, 221-231.
Diggle et al., Anodic oxide films on aluminum, Chem. Rev. 1969, 69, 365-405.
Fray et al., Extracellular glucose turnover in the striatum of unanaesthetized rats measured by quantitative microdialysis, J. Physiol. 1997, 504, 721-726.
Hashimoto et al., Effects of N-methyl-D-aspartate, kainate or veratridine on extracellular concentrations of free D-serine and L-glutamate in rat striatum: an in vivo microdialysis study, Brain Res. Bull. 2000, 53, 347-351.
Herrera-Marschitz et al., On the origin of extracellular glutamate levels monitored in the basal ganglia of the rat by in vivo microdialysis, J. Neurochem. 1996, 66, 1726-1735.
Hsieh et al., On-chip microdialysis system with flow-through glucose sensing capabilities, J. Diabetes Sci. Technol. 2007, 1, 375-383.
Jina et al., Design, development, and evaluation of a novel microneedle array-based continuous glucose monitor, J. Diabetes Sci. Technol. 2014, 8, 483-487.
Kanamori et al., Quantitative determination of extracellular glutamine concentration in rat brain, and its elevation in vivo by system A transport inhibitor, alpha-(methylamino)isobutyrate, J. Neurochem. 2004, 90, 203-210.
Kotake et al., A flexible parylene neural probe combined with a microdialysis membrane, Int. Conf. Miniaturized Syst. Chem. Life Sci., 12th 2008, 1687-1689.
Lada et al., Quantitative in vivo monitoring of primary amines in rat caudate nucleus using microdialysis coupled by a flow-gated interface to capillary electrophoresis with laser-induced fluorescence detection, Anal. Chem. 1996, 68, 2790-2797.
Lebouitz et al., Vacuum encapsulation of resonant devices using permeable polysilicon, IEEE Int. Conf. Micro Electro Mech. Syst., 12th; IEEE, 1999, 470-475.
Lee et al., Dissolving microneedles for transdermal drug delivery, Biomaterials 2008, 29, 2113-2124.
Lee et al., A new thin silicon microneedle with an embedded microchannel for deep brain drug infusion, Sensors and Actuators B, 2015, 209, 413-422.
Lee et al., Microfabricated sampling probes for in vivo monitoring of neurotransmitters, Anal. Chem. 2013, 85, 3828-3831.
Lee et al., Microfabricated sampling probes for in vivo monitoring of neurotransmitters, Anal. Chem., 85(8):3828-31 (Apr. 2013).
Leichle et al., Integration of lateral porous silicon membranes into planar microfluidics, Lab Chip, 8 pp., 2014.
Li et al., An optimized hollow microneedle for minimally invasive blood extraction, Biomed. Microdevices 2013, 15, 17-25.
Menacherry et al., In vivo calibration of microdialysis probes for exogenous compounds, Anal. Chem. 1992, 64, 577-583.

(56) References Cited

OTHER PUBLICATIONS

Metz et al., Flexible microchannels with integrated nanoporous membranes for filtration and separation of molecules and particles, IEEE Int. Conf. Micro Electro Mech. Syst., 15th; IEEE, 2002, 81-84.
Molchanova et al., Characteristics of basal taurine release in the rat striatum measured by microdialysis, Amino Acids 2004, 27, 261-268.
Poinern et al., Progress in nano-engineered anodic aluminum oxide membrane development, Materials 2011, 4, 487-526.
Popat et al., Surface modification of nanoporous alumina surfaces with poly(ethylene glycol), Langmuir 2004, 20, 8035-8041.
Shackman et al., Microdialysis coupled on-line to capillary liquid chromatography with tandem mass spectrometry for monitoring acetylcholine in vivo, J. Neurosci. Methods 2007, 159, 86-92.
Slaney et al., Push-pull perfusion sampling with segmented flow for high temporal and spatial resolution in vivo chemical monitoring, Anal. Chem. 2011, 83, 5207-5213.
Smith et al., Quantitative microdialysis of dopamine in the striatum: effect of circadian variation, J. Neurosci. Methods 1992, 44, 33-41.
Song et al., Electrophoretic concentration of proteins at laser-patterned nanoporous membranes in microchips, Anal. Chem. 2004, 76, 4589-4592.
Song et al., Microchip dialysis of proteins using in situ photopatterned nanoporous polymer membranes, J. Anal. Chem. 2004, 76, 2367-2373.
Song et al., In vivo neurochemical monitoring using benzoyl chloride derivatization and liquid chromatography-mass spectrometry, Anal. Chem. 2012, 84, 412-419.
Song et al., Mass spectrometry "sensor" for in vivo acetylcholine monitoring, Anal. Chem. 2012, 84, 4659-4664.
Song et al., Reactions in droplets in microfluidic channels, Angew. Chem., Int. Ed. Engl., 2006, 45, 7336-7356.
Striemer et al., Charge- and size-based separation of macromolecules using ultrathin silicon membranes, Nature 2007, 445, 749-753.
Suh et al., Highly ordered two-dimensional carbon nanotube arrays, Appl. Phys. Lett. 1999, 75, 2047-2049.
Trautmann et al., Pore geometry of etched ion tracks in polyimide, Nucl. Instrum. Methods Phys. Res., B 1996, 111, 70-74.
Tucci et al., Glutamate measured by 6-s resolution brain microdialysis: capillary electrophoretic and laser-induced fluorescence detection application, J. Chromatogr. B Biomed Sci. Appl., 1997, 694, 343-349.
Verhoeven et al., Applying ceramic nanoporous microneedle arrays as a transport interface in egg plants and an ex-vivo human skin model, Microelectronic Engineering, 2012, 98, 659-662.
Wang et al., Collection of nanoliter microdialysate fractions in plugs for off-line in vivo chemical monitoring with up to 2 s temporal resolution, J. Neurosci. Methods 2010, 190, 39-48.
Wang et al., Collection, storage, and electrophoretic analysis of nanoliter microdialysis samples collected from awake animals in vivo, Anal. Bioanal. Chem. 2011, 400, 2013-2023.
Watson et al., In vivo measurements of neurotransmitters by microdialysis sampling, Anal. Chem. 2006, 78, 1391-1399.
Wu et al., High aspect ratio etching of nanopores in PECVD SiC through AAO mask, IEEE Int. Conf. Nano/Micro Eng. Mol. Syst., 8th; IEEE, 2013, 986-989.
Yang et al., Determination of extracellular glutathione in livers of anaesthetized rats by microdialysis with on-line high-performance liquid chromatography, J. Chromatogr. B Biomed. Appl., 1995, 667, 41-48.
Zahn et al., Microdialysis microneedles for continuous medical monitoring, Biomed. Microdevices, 7(1):59-69 (2005).

\* cited by examiner

A)

B)

MICROFABRICATION OF A MICRODIALYSIS PROBE WITH NANOPOROUS MEMBRANE

CROSS REFERENCE TO RELATED APPLICATIONS

This application is a U.S. National Phase Application under 35 U.S.C. 371 of International Application No. PCT/US2016/063930 filed on Nov. 29, 2016 and published in English as WO 2017/100028 A1 on Jun. 15, 2017. This application claims the benefit of priority from U.S. Provisional Application No. 62/264,465, filed on Dec. 8, 2015. The entire disclosures of all of the above applications are incorporated herein by reference.

GOVERNMENT SUPPORT

This invention was made with Government support under EB003320 awarded by the National Institutes of Health. The U. S. Government has certain rights in this invention.

BACKGROUND

This section provides background information related to the present disclosure which is not necessarily prior art.

Microdialysis is widely used for in vivo sampling. In this technique, a semi-permeable membrane probe is inserted into tissue or fluid and perfused with an isotonic solution. Chemicals in the tissue diffuse across the membrane according to their concentration gradient and are collected in fractions for analysis. The popularity of microdialysis stems from its favorable properties. Samples are continuously removed from a well-defined space without net fluid loss from the tissue. The membrane prevents large molecules and debris from being collected that might interfere with downstream assays. Collection of a series of fractions allows changes in tissue chemistry to be monitored over time. The probe can also be used for local delivery of chemicals. Microdialysis is versatile because it can be used to sample from organs, tissues, tumors, and body fluids.

Despite the advantages, the size of microdialysis probes creates some limitations. Probes are generally made by coupling capillaries to preformed dialysis tubing resulting in a cylindrical shape with a diameter defined by the dialysis tubing, typically no smaller than 220 µm. The relatively large probe diameter prevents sampling from microenvironments such as small brain nuclei. This problem is especially acute in smaller subjects, like mice, which are often preferred for research because of the extensive genetic tools and models available. Tissue damage with potentially confounding effects on measured chemicals is another issue that is likely worse with larger diameter probes. Finally, in clinical applications, smaller probes are desirable to minimize discomfort and increase precision.

A route to miniaturizing microdialysis probes is by microfabrication. Microfabricated needles without membranes have been applied for drug delivery and sampling. We have reported a 70 µm wide by 85 µm thick microfabricated "push-pull" probe for in vivo sampling. (Lee et al., *Anal. Chem.* 2013, 85, 3828-3831) Sampling occurred by pulling fluid through one channel while pushing an equal volume out the other at 50 nL/min. A limitation of push-pull and needle-type sampling is that proteins and debris can enter the sampling channel potentially interfering with assays or clogging channels. Another issue is that pull-flow connections must be made at the probe. The pull connection complicates sample collection, especially at the low sampling rates used. This plumbing requirement is in contrast to microdialysis where fluids are pumped into the inlet leaving the outlet free for sample collection. Finally, the push and pull flows must be balanced to avoid net fluid loss or gain around the probe. Fluid balancing is challenging at such low flow rates but is not necessary in microdialysis.

A key challenge in microfabricating a microdialysis probe is forming a membrane over an open channel. For example, microdialysis probes have been fabricated in Si with permeable polysilicon or fabricated pores as the permeable layer. (Zahn et al., *Biomed. Microdevices* 2005, 7, 59-69; Desai et al., *J. Membr. Sci.* 1999, 159, 221-231; Lebouitz et al., *IEEE Int. Conf. Micro Electro Mech. Syst*, $12^{th}$, IEEE, 1999, 470-475) But the polysilicon membrane was too fragile to use with pressure-driven fluid flows in microchannels. Microfabricated dialysis probes with high pore density and suitable recovery have yet to be demonstrated for in vivo sampling.

SUMMARY

This section provides a general summary of the disclosure, and is not a comprehensive disclosure of its full scope or all of its features.

A procedure has been developed to microfabricate a microdialysis probe in Si. The membrane is formed by electrochemical etching of a porous anodic aluminum oxide (AAO) layer to yield a high density of straight pores with controllable size. The porous AAO is used as a mask for deep reactive ion etching (DRIE) of a polysilicon layer that is underneath the AAO and over a microfluidic channel. Utility of the probes is demonstrated by monitoring neurotransmitters in the brain of live animals.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

Figure 15:
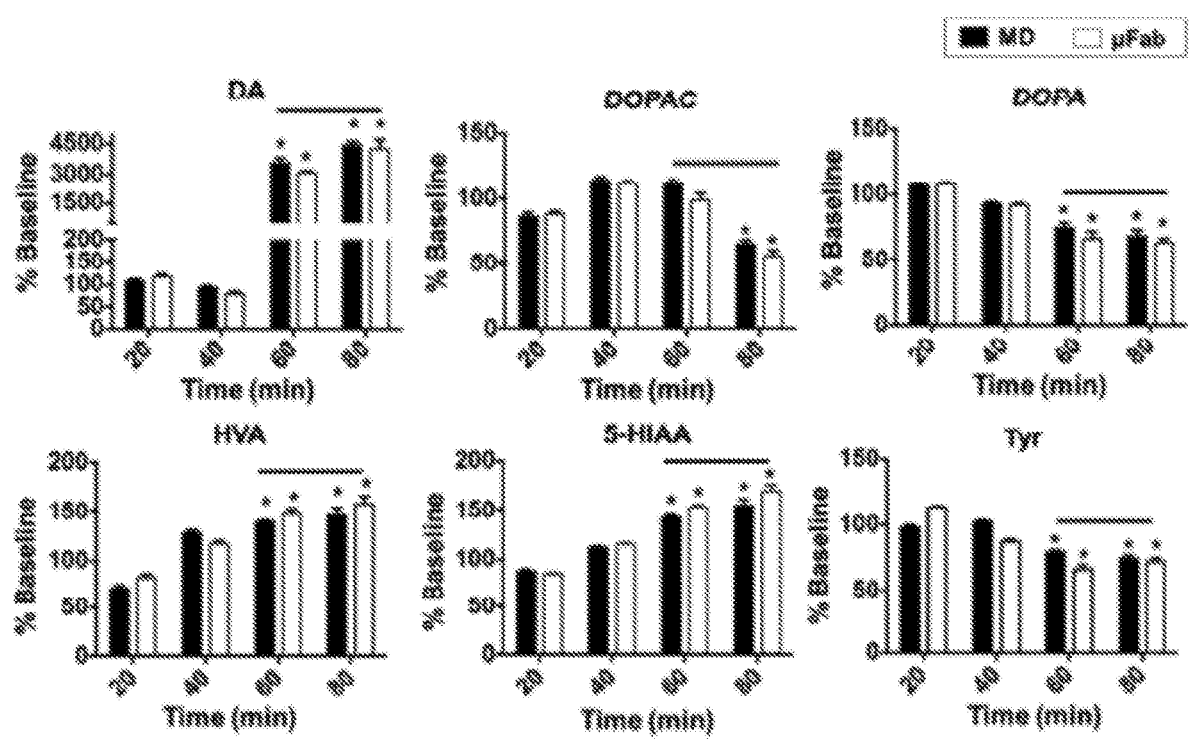

FIG. 15 illustrates dual probe microdialysis of rat striatum showing effects of AMPH (5 mg/kg, IP) on DA release and other neurochemicals sampled by a concentric microdialysis probe (MD) and microfabricated probe (μFab). Both probe types have similar performance on response to dynamic in vivo chemical changes. Lines indicates when AMPH was present (fractions at 60 and 80 min). Data were converted to percent of baseline measurement to normalize pre-drug levels to 100 percent. Student's t-test indicates a significant change (*p<0.05) between basal and post drug levels. Results are the mean±SEM, n=3 animals. For other measured neurochemicals, their post drug levels did not significantly change.

Figure 16:
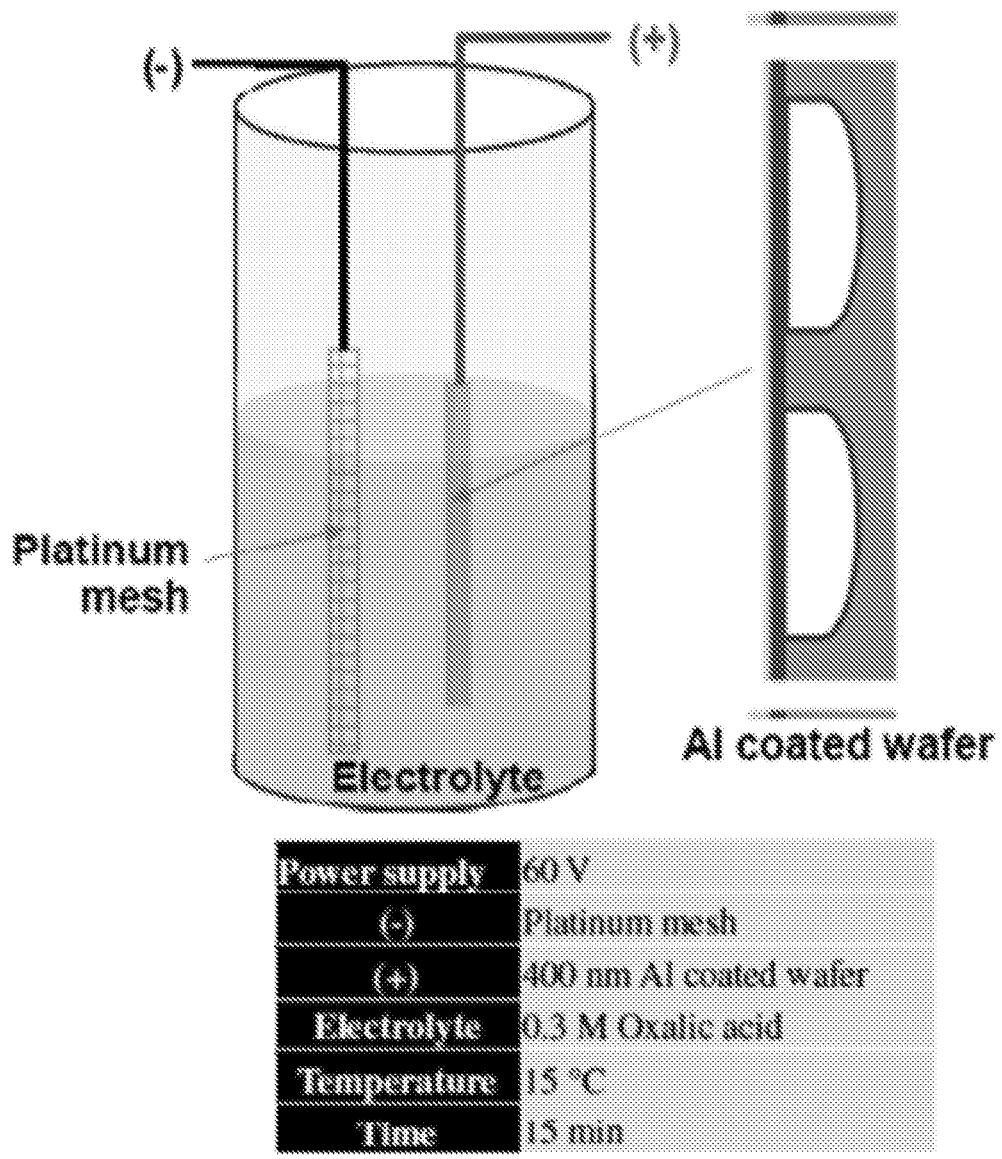

FIG. 16 illustrates the overall setup of an anodized aluminum oxide (AAO) process for generating pores through an Al layer. After deposition of 400 nm Al layer over the wafer, the Al coating was anodized at 60 V in 0.3 M oxalic acid for 15 min at 15° C. Platinum mesh was used as a counter electrode, which was aligned parallel to the Al coated wafer. The device wafer was facing toward and 1 inch apart from the platinum mesh.

Figure 17:
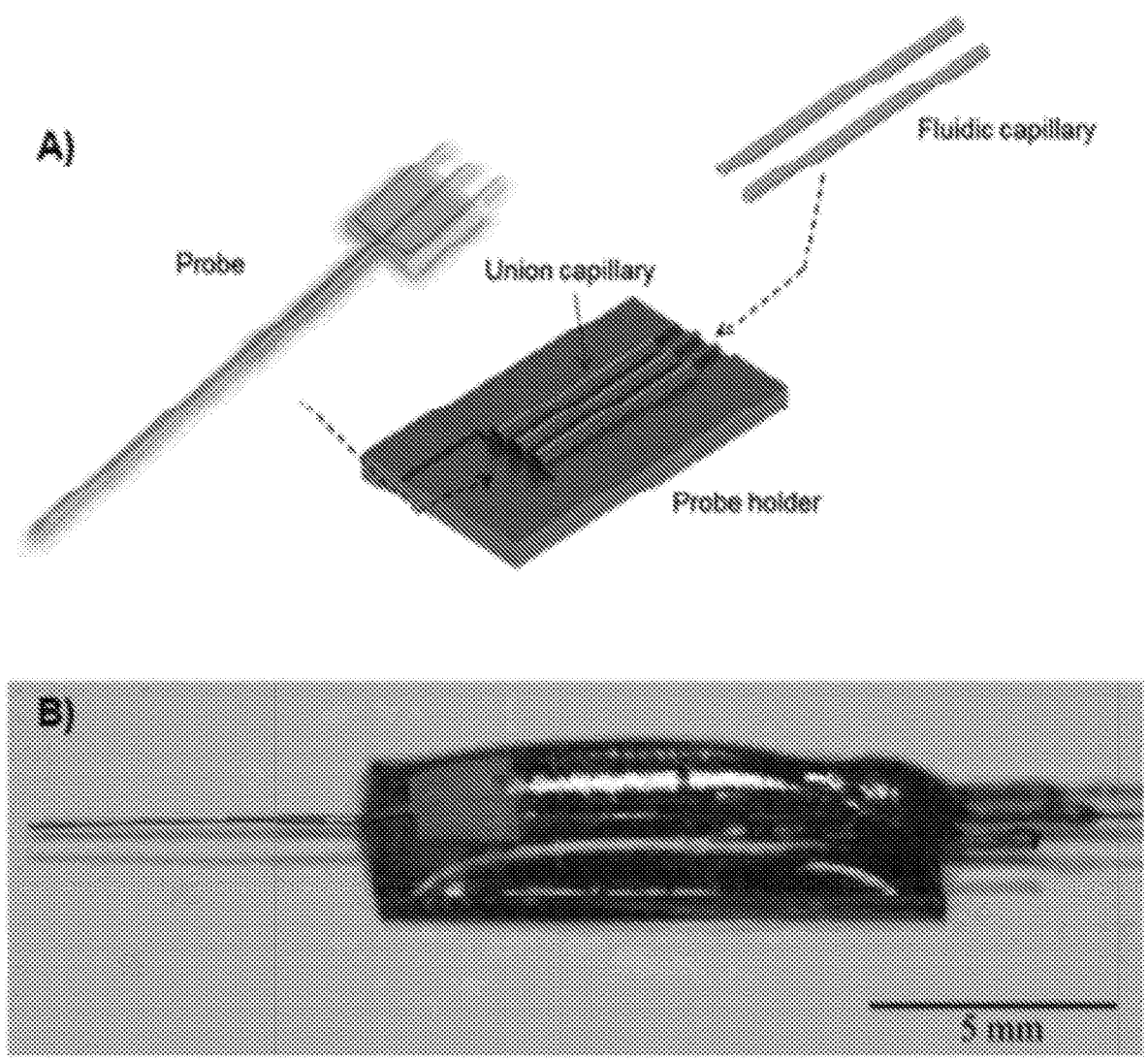

FIG. 17 illustrates fabrication of a Probe Holder. The probe holder has guides to connect probe ports and capillaries. Probe holders were fabricated from a silicon wafer with growth of a 1 μm silicon dioxide layer. The 2 mm wide rectangle for a guide of probe connection ports was patterned by lithography and $SiO_2$ layer was removed by BHF. A second lithography step was performed to pattern 360 μm wide trenches for a guide of capillaries and DRIE etched 50 μm deep. Photoresist on the wafer was removed by positive resist stripper (PRS 2000; Avantor Performance Materials, Pa.) and 40 μm deep trenches and rectangles were additionally etched by DRIE. To connect fluidic capillaries to microchannels in a probe, a union capillary of 1 cm length with 180 μm ID and 360 μm OD was glued on the guiding trenches of a probe holder with epoxy gel resin. (A) Probe ports were inserted into union capillaries and 12 cm length of 100 μm ID and 150 μm OD fluidic capillaries were joined to inlet and outlet probe ports through the union capillary. Finally, all assembled devices were sealed with epoxy gel resin. The probe glued to the holder as shown in (B).

Figure 18:
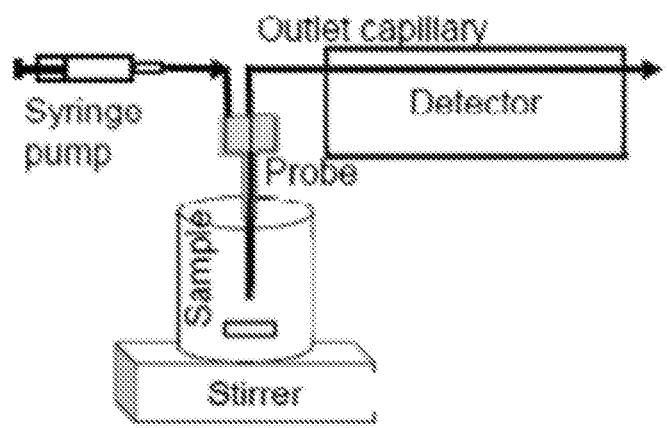
Figure 18:
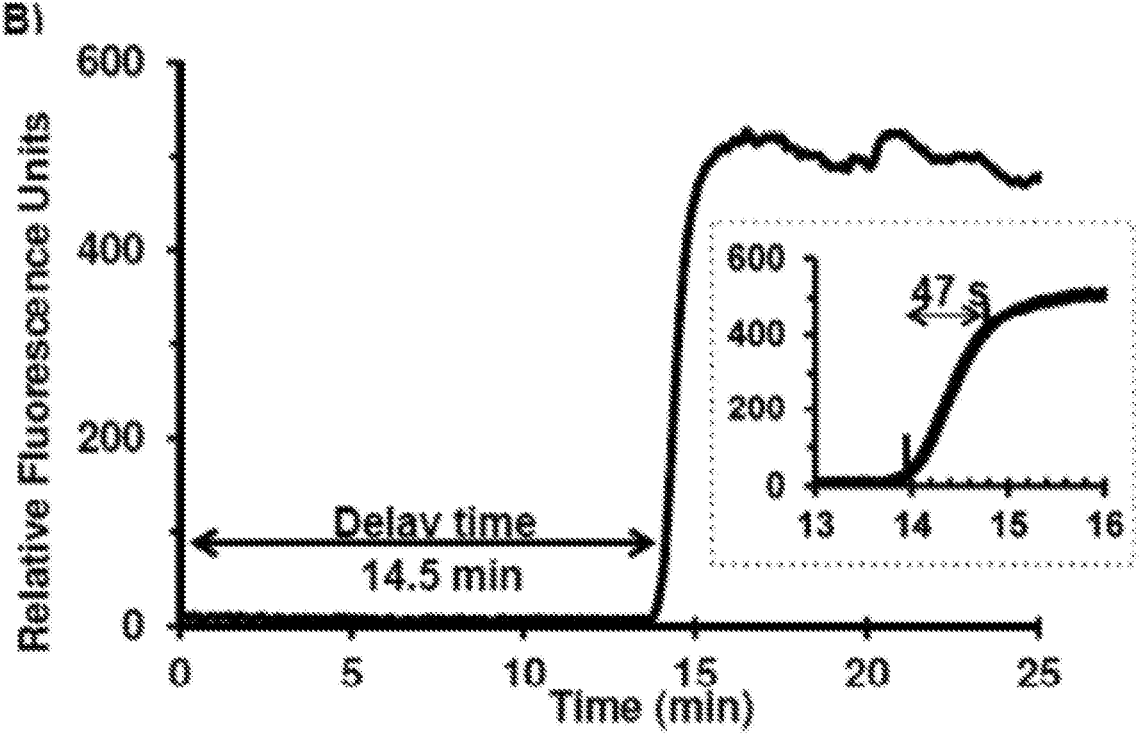

FIG. 18 depicts the dynamic response time of the microfabricated probe to step change in sampled concentration. (A) Illustration of experimental setup. Probe was inserted into a solution of water and then switched to a solution of 50 μM fluorescein as the sample. Fluorescence was monitored downstream on the outlet capillary. (B) Trace shows representative example for detection fluorescent change with time beginning at switch. Delay time is 14.5 min, which corresponds to the internal volume of ~1400 nL at the perfusion rate of 100 nL/min. Inset shows the 10% to 90% response time. Average was 47±2 s (n=7).

Figure 19:
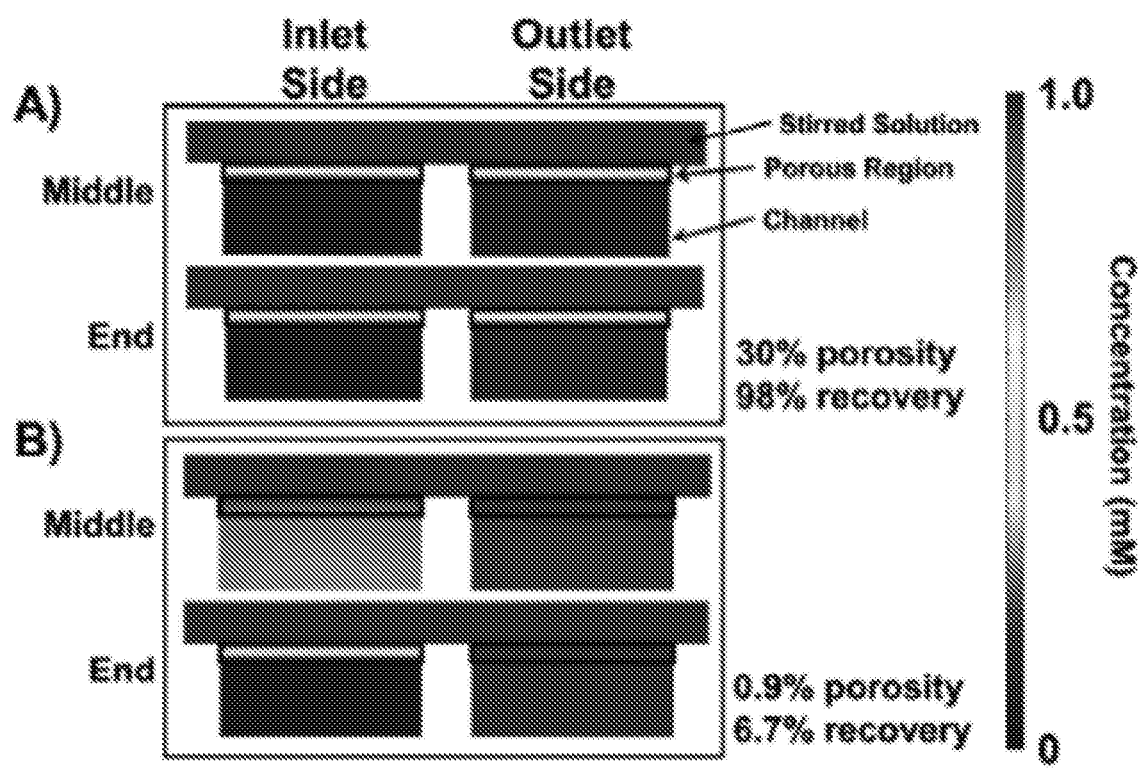

FIG. 19 illustrates modeling and simulation of 1 mM dopamine flowing through the microfabricated probe. The microfabricated probe was constructed in COMSOL Multiphysics 4.4 (Burlington, Mass.) to model its recovery. The fabricated probe has semi-circular fluidic channels; but for ease of modeling, the channels were designed as 60 μm×24 μm rectangles which gave the same cross-sectional area as the actual probes. The total length of the channels was 8 mm in a 'U' shape like the actual probe. The porous membrane was designed as a polysilicon rectangle, 5 μm×60 μm, overlaid the channels. A large box was connected to the external boundary of the membrane region for simulating the probe in a well-stirred solution. The 'Free and Porous Media Flow' and 'Species Transport in Porous Media' physics models were applied to the channel and membrane regions. Navier-Stokes equations modeled the fluid (water) in the open channel with a flow rate of 100 nL/min. Fluid movement in the porous region was defined by the Brinkman equation and a permeability of 50 $nm^2$ was used. The porosity variable was modified to match experimental data. For the transport of chemical species, the diffusion coefficient of dopamine, $6 \times 10^{-10}$ $m^2$/s was used[†]. The exterior probe volume used 'Laminar Flow' and 'Transport of Diluted Species' physics with a flow rate of 10 mL/min to simulate a well-stirred solution. Images below show cross section of probe at the middle and end of the probe color coded for DA concentration. A) Recovery for probe with 30% porosity and B) for 0.9% porosity.

Figure 20:
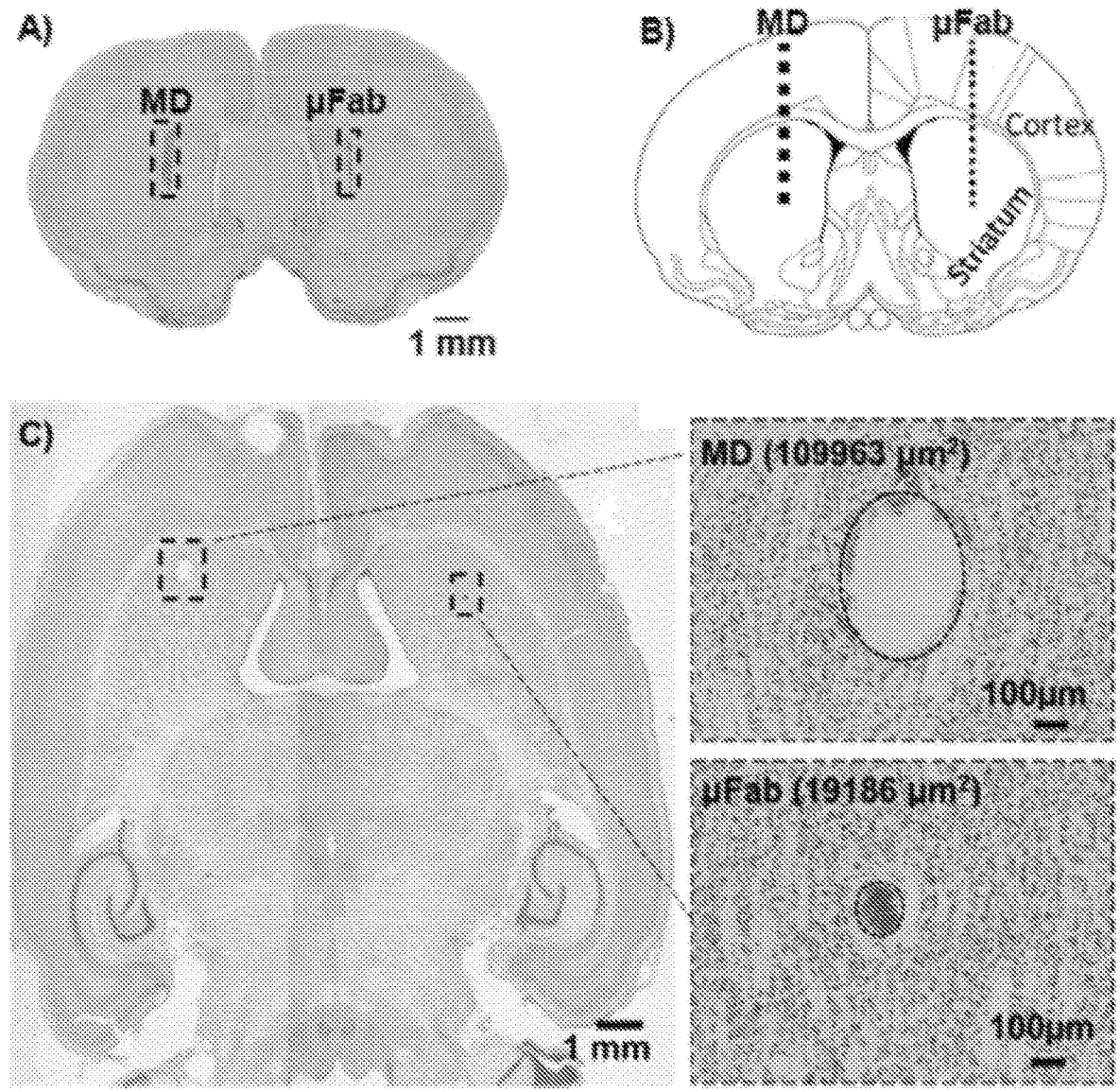

FIG. 20 illustrates histology that indicates probe placements and minimized tissue displacement. A) The brain was implanted bilaterally by a conventional dialysis probe (left) and the microfabricated probe (right). The brain was cut into 40 μm coronal sections and Nissl stained to show overall brain structure with probe tracts (boxes with dashed line). B) Dotted lines indicates tracts overlaid on a rat brain atlas diagram, corresponding to (A). C) Horizontal section of the brain. The zoomed in images in the insets indicates the probe tract areas of both probes. As shown, the μFab probe tract is 83% smaller than the MD probe tract.

DETAILED DESCRIPTION

Example embodiments will now be described more fully with reference to the accompanying drawings.

In one embodiment, a method for forming a dialysis membrane over a microfluidic channel involves forming a polysilicon layer over the channel, depositing a layer of aluminum over the polysilicon layer, and then anodizing the aluminum layer to make a layer of porous anodized aluminum oxide that is a mask on top of the underlying polysilicon layer. Finally, holes are formed in the polysilicon layer by deep reactive ion etching through the pores of the porous anodized aluminum oxide mask to make the dialysis membrane covering the microfluidic channel. In various embodiments, the microchannel is formed at the surface of a silicon body. In preferred embodiments, the silicon body is produced from a wafer of crystalline polysilicon.

Other embodiments involve the further steps of removing the porous anodized aluminum oxide mask and depositing a fresh layer of aluminum. Then the fresh layer of aluminum is anodized in order to provide a fresh layer of porous anodized aluminum oxide. Advantageously, the fresh layer of aluminum and the fresh layer of porous anodized aluminum oxide have a thickness greater than the thickness of the porous anodized aluminum oxide mask originally formed on top of an underlying polysilicon layer described above.

The product of the methods in various embodiments provide a microdialysis probe made of a unitary block of material and comprising, from a proximal end to a distal end, a body, a support shank, a shank, and a tip. An illustrative embodiment is given in FIG. 1. The body comprises an inlet port and an outlet port. Finally, the probe further comprises a single channel in the surface of the probe that runs from the inlet port through the shank, through the body, through the support shank, and through the shank to the tip and back to the outlet port. A nanoporous layer covers the channel in at least part of the shank and a solid layer covers the channel everywhere that the porous layer does not cover the channel. In preferred embodiments, the path of the channel is straight with a U-shape turn at the tip. The probe is dimensioned to be used in small spaces. Optionally, the tip of the probe is pointed to facilitate entry of the probe into a tissue.

In various embodiments, the overall length of the probe is from 2 to 11 mm. In illustrative embodiments, the thickness of the shank is 10 to 40 microns and other parts (i.e., the body and support shank) have the same thickness as, or a greater thickness than, the thickness of the shank. In further illustrative embodiments, the width of the shank is 30 to 180 microns. The depth of the channel ranges from 5 to 35 microns and the width of the channel ranges from 5 to 65 microns, in various embodiments.

In preferred embodiments, the solid layer that covers the channel everywhere that the porous layer does not cover the channel, is formed of polysilicon. The porous layer, on the other hand, is made of a polysilicon layer, a layer of anodized aluminum oxide, or a layer of polysilicon and a layer of anodized aluminum. In the case of the latter, in an embodiment the polysilicon layer covers the channel and is in contact with the silicon probe, and the anodized aluminum oxide layer is disposed on top of the polysilicon layer. In various embodiments, the porous layer has a thickness of 1 to 10 microns. In these or other embodiments, the porous layer covers a 0.1 to 8 mm length of the shank, and covers at least a part of the channel. The unitary body from which the probe is made is preferably of crystalline silicon.

The microfabricated probes are used in dialysis. In non-limiting fashion, a method of identifying or sampling molecules in a fluid involves inserting the tip and at least a part of the shank of a probe, as described herein, into the fluid and then flowing a solution from the inlet port of the probe through the channel and back to the outlet port while the probe is inserted into the fluid. A fraction or fractions of the solution are collected as it emerges from the outlet port. A collected fraction can then be analyzed for the presence of the molecule. In preferred dialysis procedures, the solution and the fluid are isotonic.

The probes are also useful for reverse dialysis. In this way, a method for delivering molecules into a fluid involves inserting the tip and at least a part of the shank covered by the porous membrane of the probes described herein into the fluid and flowing a solution from the inlet port of the probe through the channel and back to the outlet port while the probe is inserted into the fluid. Here, the solution has a higher concentration of the molecule than is found in the fluid and the molecules pass by dialysis from the solution through the membrane into the fluid. The solution and the fluid are preferably isotonic.

The term fluid is used for all compositions or systems that are analyzed using the inventive microdialysis probes. It includes solutions and suspensions in water and other solvents, and also includes physiological fluids like blood. In addition, the term covers any biological tissue, such as organs and organ preparations, intercellular fluid in the brain and other organs, and the like.

Figure 1:
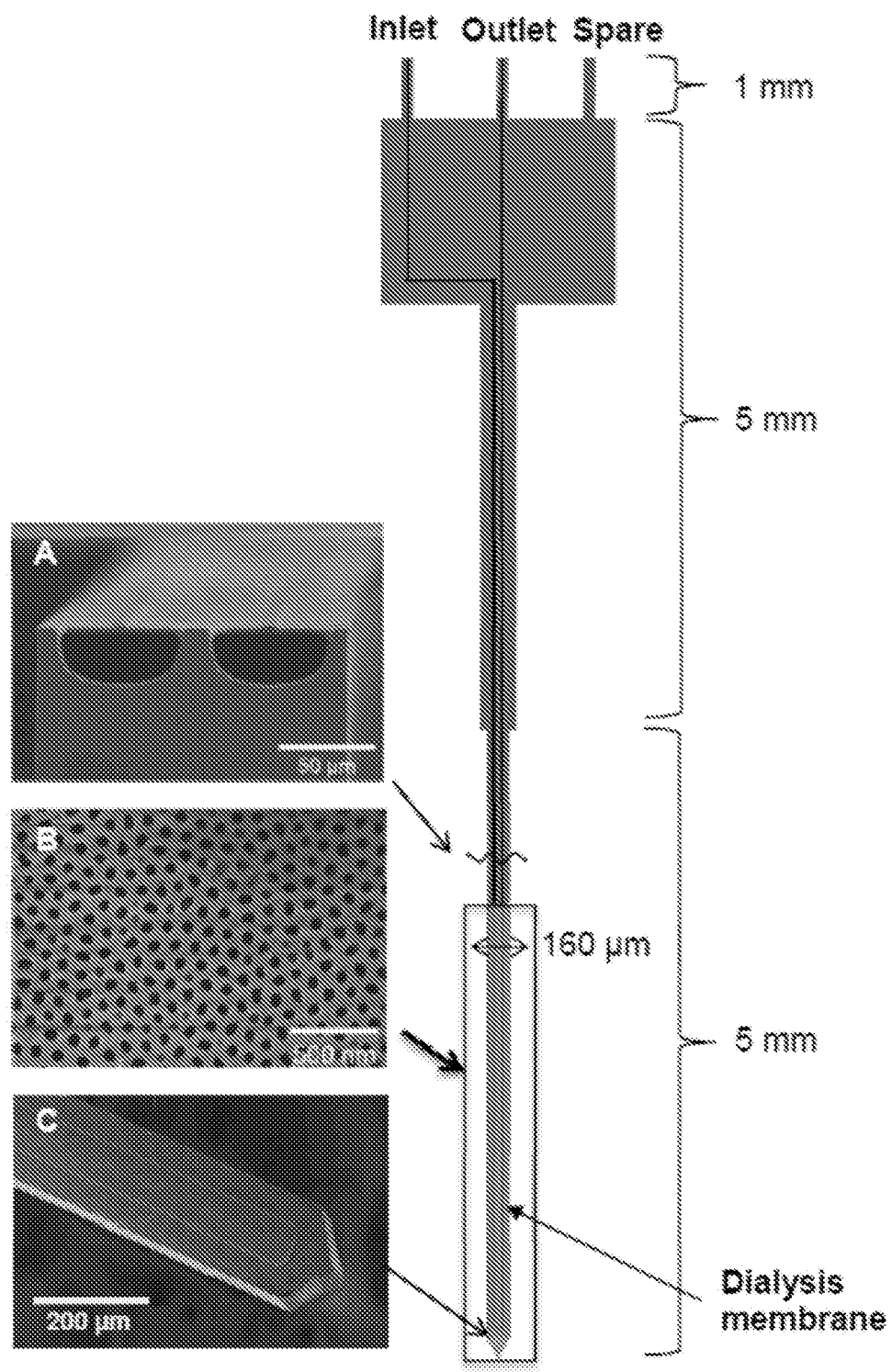
FIG. 1 shows a layout of a sample microfabricated microdialysis probe. A probe has 3 ports including inlet, outlet, and spare for other potential uses (it was not used at this probe). (A) Scanning electron microscope (SEM) image of cross-section of channels showing semicircular shape and thin polysilicon top layer. (B) SEM image of AAO membrane over sampling area. (C) SEM image of sampling probe tip showing the channel pattern.

An embodiment of the probe is shown in FIG. 1. The drawing shows the overall probe shape. Inset micrograph A shows how the channels are disposed in the shank of the probe. Micrograph B shows a top view of the porous membrane covering a portion of the shank. Inset C of FIG. 1 shows a detail of the probe tip. The outline of the channel path is shown. The white bar in inset A is 50 μm. The white bar in inset B is 500 μm and in C is 200 μm.

In various embodiments, the overall dimensions of a probe are as follows. The overall length is from 2 to 11 mm and the probe shank length is from 1 to 10 mm. The support shank length is from 1 to 10 mm. The support shank can be the same width as or wider than the shank. The shank width is from 30 to 180 microns. The shank thickness is from 10 to 40 microns and other parts of the probe may be the same or thicker.

The probe contains a channel that connects the inlet and outlet ports of the probe. The path of the channel is such that goes near the probe tip (e.g. within 1 μm of the tip) so that a portion of the channel is under the porous layer. The channel path may be straight with a U-shape turn at the tip or may have any number of bends or deviations before reaching the outlet port. The channel is from 5 to 35 microns deep and from 5 to 65 microns wide. The channel is covered with a solid layer of material, e.g., polysilicon, that is 1 to 5 microns thick, except for the membrane-covered region.

In illustrative embodiments, a porous layer (a nanoporous membrane) covers a 0.1 to 8 mm length of the shank including over the channel. In these and other embodiments, the porous layer has a plurality of pores having a diameter or dimension of 50 to 100 nm. Diameter can be used to describe the dimension of the pores because the pores are approximately circular. In the case of pores having a shape that is slightly off circular, diameter is to be understood as the shortest dimension across the nanopore. In various embodiments the nanoporous membrane comprises anodized aluminum oxide and comprises pores straight through the membrane. The pores in preferred embodiments are present at a density of $8\pm2\times10^{13}$ per square meter. For example, the overall porosity is 16 to 70 percent where the porosity is defined as the ratio of the area of the pores to the area of the membrane. The membrane is made of polysilicon or anodized aluminum oxide. The membrane is 1 to 10 microns thick in preferred embodiments.

In some embodiments, a second porous layer overlays the first porous layer. This layer has similar dimensions and porosity. Pores on the two layers may or may not be aligned to create a single pore. The materials are polysilicon or anodized aluminum oxide.

A dialysis membrane is a semi-permeable film containing various sized pores. Molecules larger than the pores cannot pass through the membrane, but small molecules can do so freely. Dialysis works by a differential diffusion across the membrane. As used here, a dialysis membrane is a semi-permeable membrane that has nanopores and that is disposed across the top of a microfluidic channel in order to seal the microfluidic channel and to provide the possibility of exchanging small molecules between a solution in the microfluidic channel and the liquid in a tissue into which a microdialysis probe, as described herein, is inserted.

A microfluidic channel is the term used to describe channels inscribed in the surface of a body such as crystalline silicon. The dimensions of the microfluidic channel are on the order of microns. The microfluidic channel runs from an inlet port through the body, support shank, and a shank to the tip and back to an outlet port of the microdialysis probe. For simplicity, the terms channel and microfluidic channel are used for the structure during all stages of construction, including when the channel is open or uncovered. In later stages of construction, the channel is "covered" or "buried" in the material of the probe so that it is bound on all sides except the inlet or outlet. In the final product, the microfluidic channel is a conduit running from the inlet port to the outlet port; part of the microfluidic channel is covered by a non-porous cover, while at least a portion of the shank is covered by a non-porous cover providing a dialysis membrane.

Polysilicon or polycrystalline silicon is a high purity polycrystalline form of silicon. Polysilicon consists of small crystals and is distinguished from monocrystalline or single crystal silicon. Polysilicon is therefore a material consisting of multiple small silicon crystals.

Anodized aluminum oxide is a material produced by subjecting an aluminum to an anodizing process. Anodizing the aluminum forms aluminum oxide with nanopores in the aluminum oxide material. The size and disposition of the nanopores in anodized aluminum oxide is such that it can be used as a mask to provide the nanoporous dialysis membrane of the probes described herein. In particular, in various embodiments, it is used as a mask during lithographic processing to form a nanoporous membrane in materials underlying the aluminum oxide.

Figure 2:
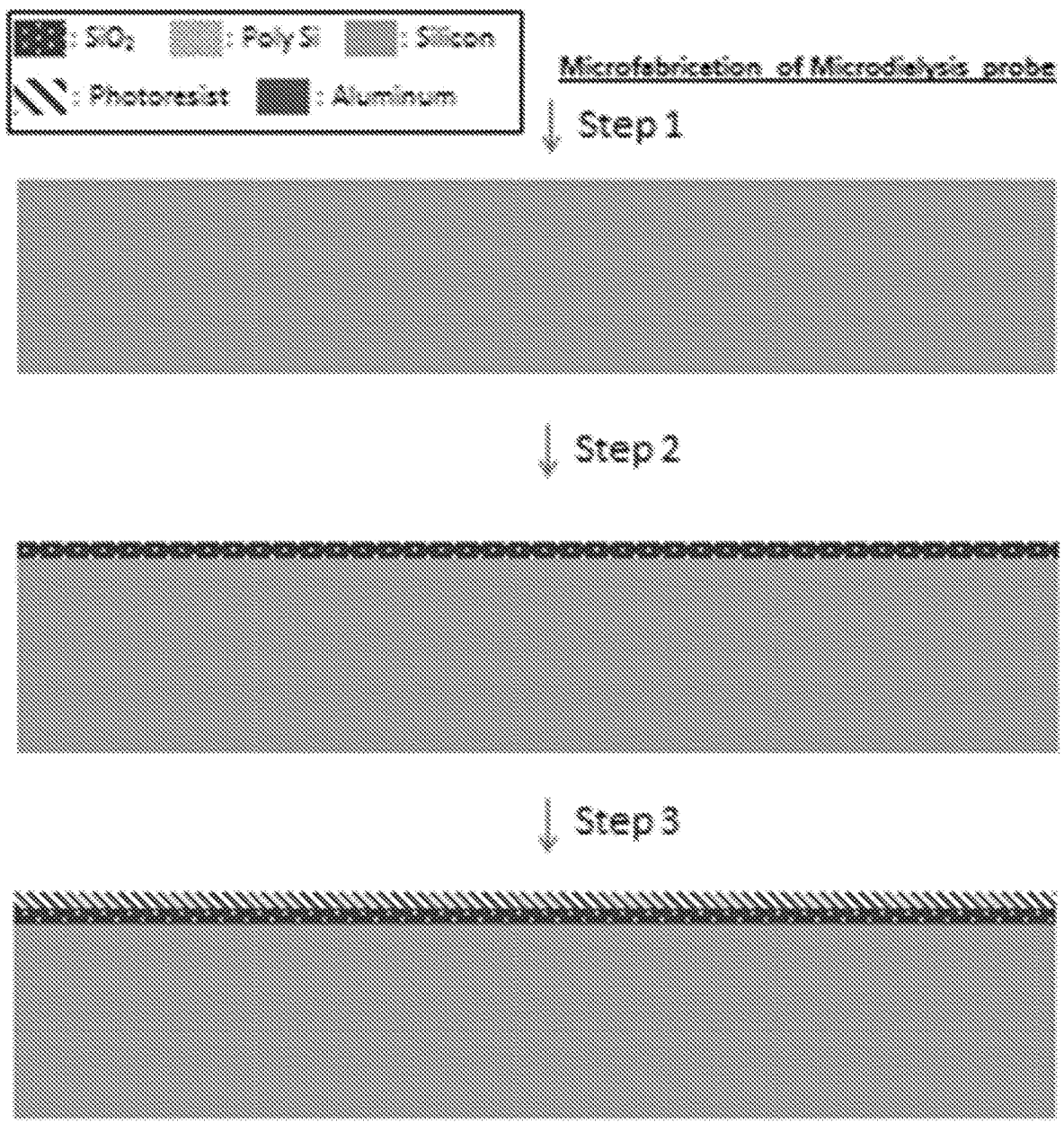
FIGS. 2-12 depict the steps of a process for making a microdialysis probe from crystalline Si.

The microdialysis probes of the current teachings are made of a body connected to a support shank connected to a shank that ends in a tip (reading from a proximal end to a distal end). As illustrated in the embodiment of FIG. 2, the body of the probe is more macro in size and provides ports for connecting the microdialysis probe to a source of some fluid and to analysis instruments. A microfluidic channel runs from the inlet port into the body, through the body and the support shank, through the shank to the tip, and returning to the outlet port in the body. As shown in FIG. 2, the support shank and shank form a needle-like body that provides, along with the tip, the ability to insert the probe into a tissue. The support shank can be wider or thicker than the shank for improved physical properties. The shank itself contains a semi-permeable dialysis membrane over at least a portion. The shank ends in a tip that is fabricated to be sharp enough to enable easy insertion into tissues to be analyzed.

The microfluidic channel runs along the surface of the microdialysis probe, from the inlet to the body, down the support shank and the shank to the tip and back. A semi-permeable dialysis membrane is provided to cover at least part of the microfluidic channel of the shank. The microfluidic channel is covered by a solid non-porous member everywhere that the nanoporous dialysis membrane does not cover.

Fabrication of the Microdialysis Probe

A process for fabricating the microdialysis probe is given in FIGS. 2 to 12, which illustrate 31 steps used to produce the probe. In steps 1-22, a polysilicon layer is formed over a microfluidic channel. In step 23, a layer of aluminum is deposited over the polysilicon layer. In step 24, the aluminum layer is anodized to make a layer of porous anodized aluminum oxide. The porous aluminum oxide is a mask on top of the underlying polysilicon silicon layer. In step 25, holes are formed in the polysilicon layer by deep reactive ion etching through the porous anodized aluminum oxide mask. In this way, a dialysis membrane covering the microfluidic channel is made. Steps 26-31 illustrate additional optional steps in fabrication.

Referring to the steps illustrated in FIGS. 2 to 12, the following details are given on the individual steps of fabricating the probes.

Step 1—RCA Cleaning of a Silicon Wafer

A 4 inch silicon wafer (Catalog number: OL1006, Silicon Valley Microelectronics, Inc.) was cleaned by using Radio Corporation of America (RCA) cleaning solution to remove a thin oxide layer, and organic and ionic contamination on the wafer surface. The first step was organic cleaning with standard clean 1 solution (5:1:1 mixture of deionized water, $NH_4OH$ (29%), and $H_2O_2$ (30%)) at 75° C. for 10 min. The wafer was rinsed with deionized water in a flushing tank for 3 min. The second step was removal of thin oxide layer with 1:10 solution of Hydrogen fluoride and deionized water at 25° C. for 30 seconds. The wafer was rinsed in a deionized water flushing tank for 3 min. The third step was ionic cleaning with solution of standard clean 2 solution (5:1:1 mixture of deionized water, HCl (39%), and $H_2O_2$ (30%)) at 75° C. for 10 min. The wafer was rinsed in a deionized water flushing tank for 3 min. The fourth step was drying with Verteq 1600 SRD Spin Rinse Dryer (SPEC Equipment) at 2000 rpm.

Step 2—Deposit $SiO_2$ Layer by Wet Oxidation

A 2 µm $SiO_2$ layer was grown on the wafer by wet oxidation using a Tempress TS 6604. Deposition time was calculated from growth rate (angstrom/min) of $SiO_2$ on the wafer and oxidation process was conducted at a flow rate of 6 standard liters per minute (SLM) of $O_2$ (10 min) in dry oxidation at 1100° C., 4.5 SLM of $H_2$ and 3.5 SLM of $O_2$ (290 min) in wet oxidation, and 6 SLM of $N_2$ anneal (10 min).

Step 3—Photoresist Coating

3 µm of SPR220 photoresist was coated on the wafer surface using a Suss MicroTec ACS 200 Photoresist Coater and Developer. Surface moisture was removed at 90° C. for 90 seconds and the wafer was then transferred to a spin coater. 3 µm of SPR 220 photoresist was coated with 3500 rpm for 30 seconds and baked at 115° C. for 90 seconds.

Step 4—Channel Patterning Under UV Light

The initial line for channel on a photomask (not shown) was loaded into a Karl Suss MA6 Mask Aligner (SUSS MicroTec AG) along with the photoresist coated wafer. Channel patterning on the photoresist was performed by exposing the wafer through the photomask under 7 sec of UV light required for SPR220 followed by a post bake at 115° C. for 90 sec. Finally, the wafer was developed in AZ® 300 MIF Developer (AZ Electronic Materials) for 1 min and rinsed in deionized water for 2 min.

Step 5—Deep Reactive Ion Etching (DRIE) of Silicon Dioxide Layer

The exposed $SiO_2$ was removed with SPTS deep reactive ion etching (DRIE) at 1 µm/min for 12 min.

Step 6—Semicircular Shaped Channels Formed by Isotropic Etching

60 µm wide semicircular shaped channels were formed using a SPTS Xactix $XeF_2$ etcher. Isotropic etching was performed on the silicon wafer with vapor pressure 3.0 Torr of $XeF_2$, 0 Torr of $N_2$ for 20 sec on each cycle and the total number of cycles was 65.

Step 7—Remove Photoresist

SPR220 photoresist on $SiO_2$ layer was removed in PRS-2000 photoresist stripper (J.T. Baker Microelectronic Materials) at 25° C. for 10 min and rinsed by deionized water for 2 min.

Step 8—Polysilicon (Poly Si) Layer Added by Low Pressure Chemical Vapor Deposition to Close the Channel After RCA cleaning (same as step 1), channels on the silicon surface were sealed with 3 µm of polysilicon by low pressure chemical vapor deposition using a Tempress TS 6604 operated at 610° C., 220 mT, and 85 standard cubic centimeters per minute of flow, yielding 5.5 nm/min of deposition rate.

Step 9—Remove Poly Si on a $SiO_2$ Layer by Deep Reactive Ion Etching

The polysilicon layer on the wafer surface was etched with DRIE until the buried $SiO_2$ layer was exposed at 2 μm/min (1 min 38 sec).

Step 10—$SiO_2$ Removal by Buffered Hydrofluoric Acid

The $SiO_2$ layer on the wafer surface was removed by treatment with buffered hydrofluoric acid (6:1 volume ratio of 40% $NH_4F$ in water to 49% HF in water) at 25° C. for 20 min.

Step 11—Reseal Channels by Depositing Layer of Polysilicon

After RCA cleaning (step 1), channels on the silicon surface were sealed by 2 μm of polysilicon using low pressure chemical vapor deposition (Tempress TS 6604) at 610° C., 220 mT, 85 standard cubic centimeters/min of flow rate and 5.5 nm/min of deposition rate.

Step 12—Deposit $SiO_2$ Layer

A 1 μm $SiO_2$ layer was deposited by low pressure chemical vapor deposition using a Tempress TS 6604 at 920° C., 330 mT, 60/120 standard cubic centimeters/min of dichlorosilane (DCS) and Nitrous Oxide ($N_2O$) flow rate and 4.7 nm/min of deposition rate.

Step 13—Apply Photoresist Coating

All processes were the same as step 3.

Step 14—Patterning and Development of 100 Micron Wide Probe Shape

All processes were the same as step 4 with a probe shape patterned photomask.

Step 15—Remove $SiO_2$ in a Probe Shape by Deep Reactive Ion Etching (DRIE)

All processes were the same as step 5.

Step 16—Remove Photoresist

All processes were the same as step 7.

Step 17—Apply Photoresist

All processes were the same as step 3.

Step 18—Patterning and Development of 160 Micron Wide Sampling Area

All processes were the same as step 4 with a sampling area patterned photomask.

Step 19—Deep Reactive Ion Etching of the Outline of the Probe to a Depth of 150 Microns Probe shape was etched by SPTS deep reactive ion etching (DRIE) at 12 μm/min for 15 min.

Step 20—Remove $SiO_2$ Layer on the Sampling Area $SiO_2$ layer on the wafer surface was removed by treatment with buffered hydrofluoric acid (a 6:1 volume ratio of 40% $NH_4F$ in water to 49% HF in water) at 25° C. for 1 min.

Step 21—Remove Photoresist

All processes were the same as step 7.

Step 22—Etch Polysilicon Layer with Deep Reactive Ion Etching (DRIE)

The 5 μm polysilicon layer on the wafer surface was etched with DRIE down to 2 μm thickness at 2 μm/min (1 min 30 sec).

Step 23—Deposit Aluminum Layer

A 400 nm Al layer was deposited over the wafer using an e-beam evaporator (Denton Vacuum) for 267 sec with 1.5 nm/min deposition rate.

Step 24—Anodize Aluminum Layer

The Al coating was anodized by applying 60 V and 15° C. in 0.3 M oxalic acid solution for 15 min with 100×100 mm platinum mesh (Alfa Aesar) as a counter electrode, which was aligned parallel to the Al coated wafer. The device wafer was facing toward and 1 inch apart from the platinum mesh. The wafer was rinsed with deionized water and then treated with 5% phosphoric acid at room temperature for 50 min to widen the pores to 60-80 nm diameter.

Step 25—DRIE the Polysilicon Layer Through the Anodized Aluminum Oxide Layer as a Mask The polysilicon layer overlying the microchannel was etched by DRIE at −15° C. for 14 min using the anodic aluminum oxide (AAO) layer as a mask.

Step 26—Remove Porous Anodized Aluminum Oxide Layer

The AAO membrane on the wafer was removed by treating with 5% phosphoric acid at 65° C. for 1 hour.

Step 27—Deposit Fresh Aluminum Layer

A fresh 3 μm Al layer was deposited using an Enerjet evaporator for 2000 sec with 1.5 nm/min deposition rate. For this step, the wafer was tilted to a 45° angle relative to the direction of the Al deposition to prevent blocking of previous etched holes on polysilicon layer by Al metal vapor.

Step 28—Anodize the Aluminum Layer to Form Porous Anodized Aluminum Oxide Layer

The Al coating was anodized at 60 V and 15° C. in 0.3 M oxalic acid solution for 45 min with 100×100 mm platinum mesh as a counter electrode in a glass beaker. The wafer was rinsed with DI water and then treated with 5% phosphoric acid at room temperature for 90 min to widen the pores (80-90 nm in diameter).

Step 29—Bond Patterned Wafer to a "Carrier Wafer"

The wafer surface with embedded AAO membrane was bonded to a carrier wafer with Crystalbond 555 (melting point: 54° C.) on a hot plate at 80° C.

Step 30—Backside Etch to a Desired Probe Thickness

The backside of the wafer was etched by DRIE until the probe thickness reached 40 μm at 3.4 μm/min (143 min) and individual probes were no longer connected on the backside.

Step 31—Release Individual Probes in Hot Water

The wafer was transferred into a beaker and individual probes were released and collected in hot water.

EXPERIMENTAL SECTION

Chemicals and Materials

Unless specified otherwise, all chemicals were purchased from Sigma Aldrich (St. Louis, Mo.) or Fisher Scientific (Fairlawn, N.J.) and were certified ACS grade or better. Solutions were prepared with HPLC-grade water or water purified by a Milli-Q system (Millipore, Mass.). Fused silica capillaries were purchased from Molex (Phoenix, Ariz.). Epoxy glues were purchased from ITW Devcon (Danvers, Mass.) and Loctite (Westlake, Ohio). Crystalbond Adhesive was purchased from Structure Probe (West Chester, Pa.). Artificial cerebrospinal fluid (aCSF) consisted of 145 mM NaCl, 2.68 mM KCl, 1.10 mM $MgSO_4$, 1.22 mM $CaCl_2$, 0.50 mM $NaH_2PO_4$, and 1.55 mM $Na_2HPO_4$, adjusted pH to 7.4 with 0.1 M NaOH. Unions for 360 μm outer diameter (OD) capillaries were purchased from Idex Health and Science (P-772, Oak Harbor, Wash.).

Microfabrication of Microdialysis Probe with Embedded Nanoporous Membrane

Overview.

The scheme for microdialysis probes was designed in L-EDIT software (Tanner EDA). All processing was performed at the Lurie Nanofabrication Laboratory at the University of Michigan. The overall probe layout is shown in FIG. 1. Probes were 11 mm long×45 μm thick with a shank that narrowed to 160 μm wide at the tip. A microchannel with semicircular cross-section (60×30 μm) ran the length of the probe to form an inlet and outlet was fabricated in the surface (FIG. 1A). A 4 mm length of the probe at the tip was made porous by DRIE though an electrochemically etched AAO membrane (FIG. 1B) that was overlaid the thin Si layer shown in FIG. 1A.

Channel Formation

This description is based on the fabrication steps illustrated in FIGS. 2 to 12.

Figure 3:
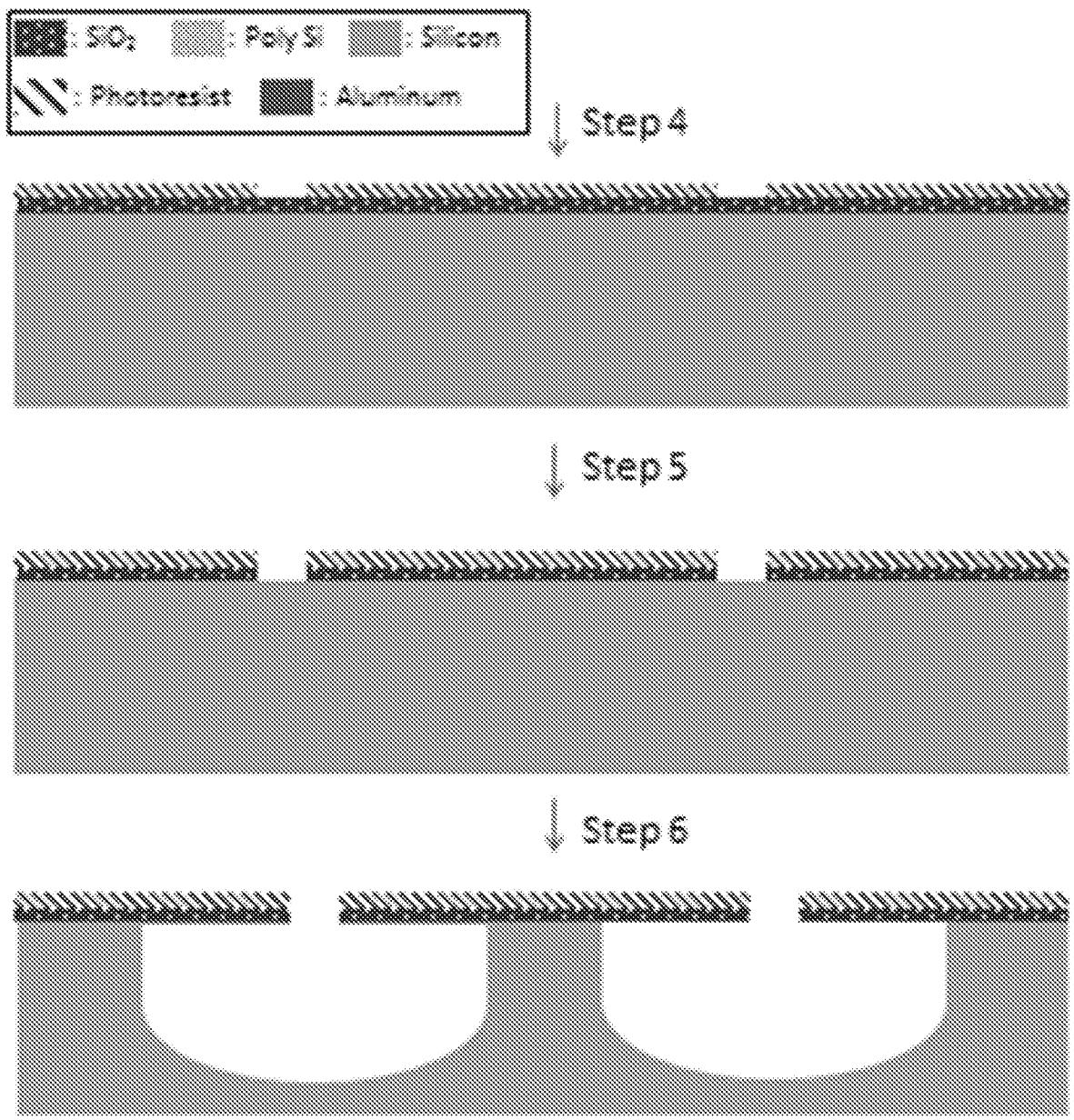
Figure 4:
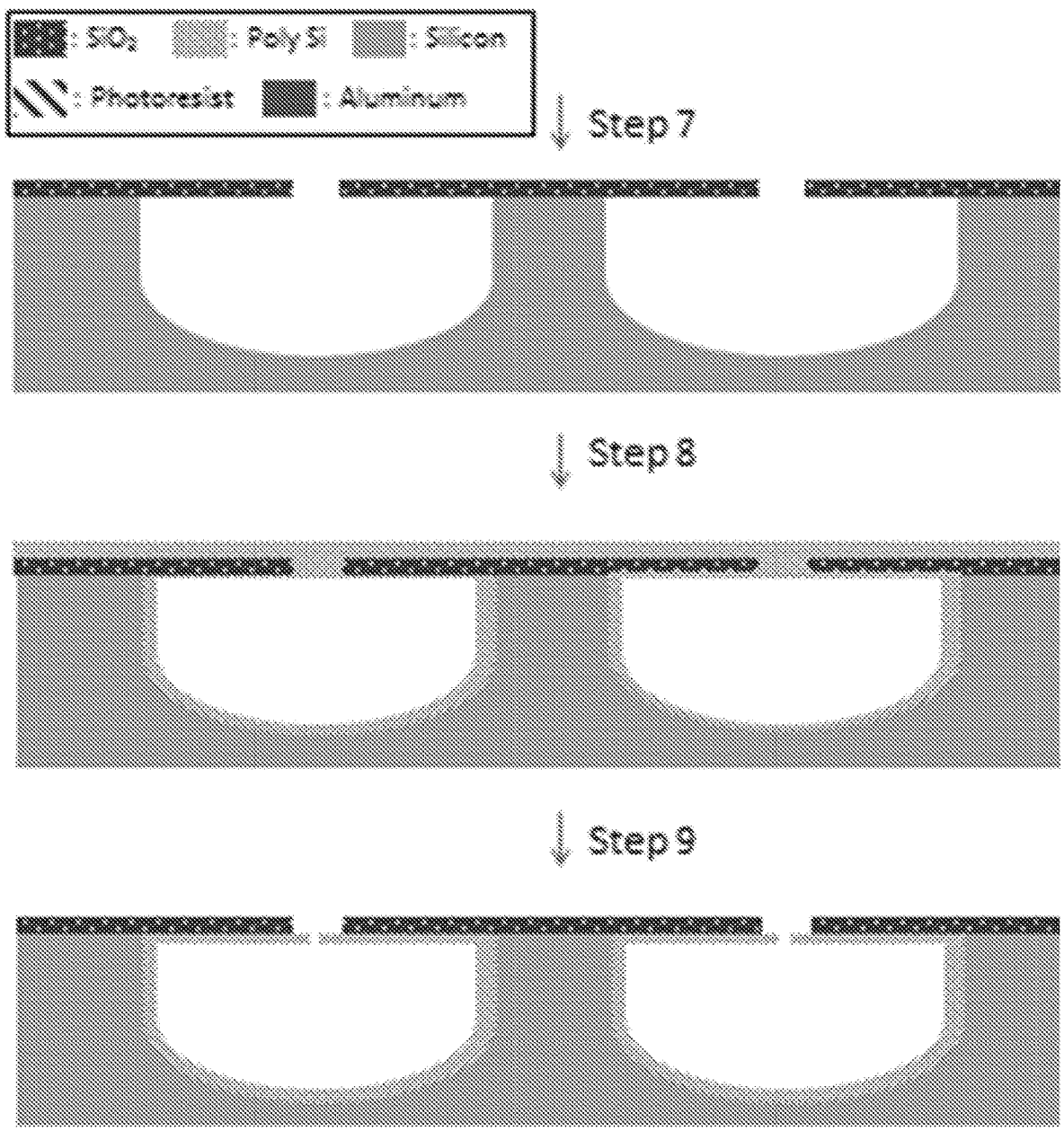
Figure 5:
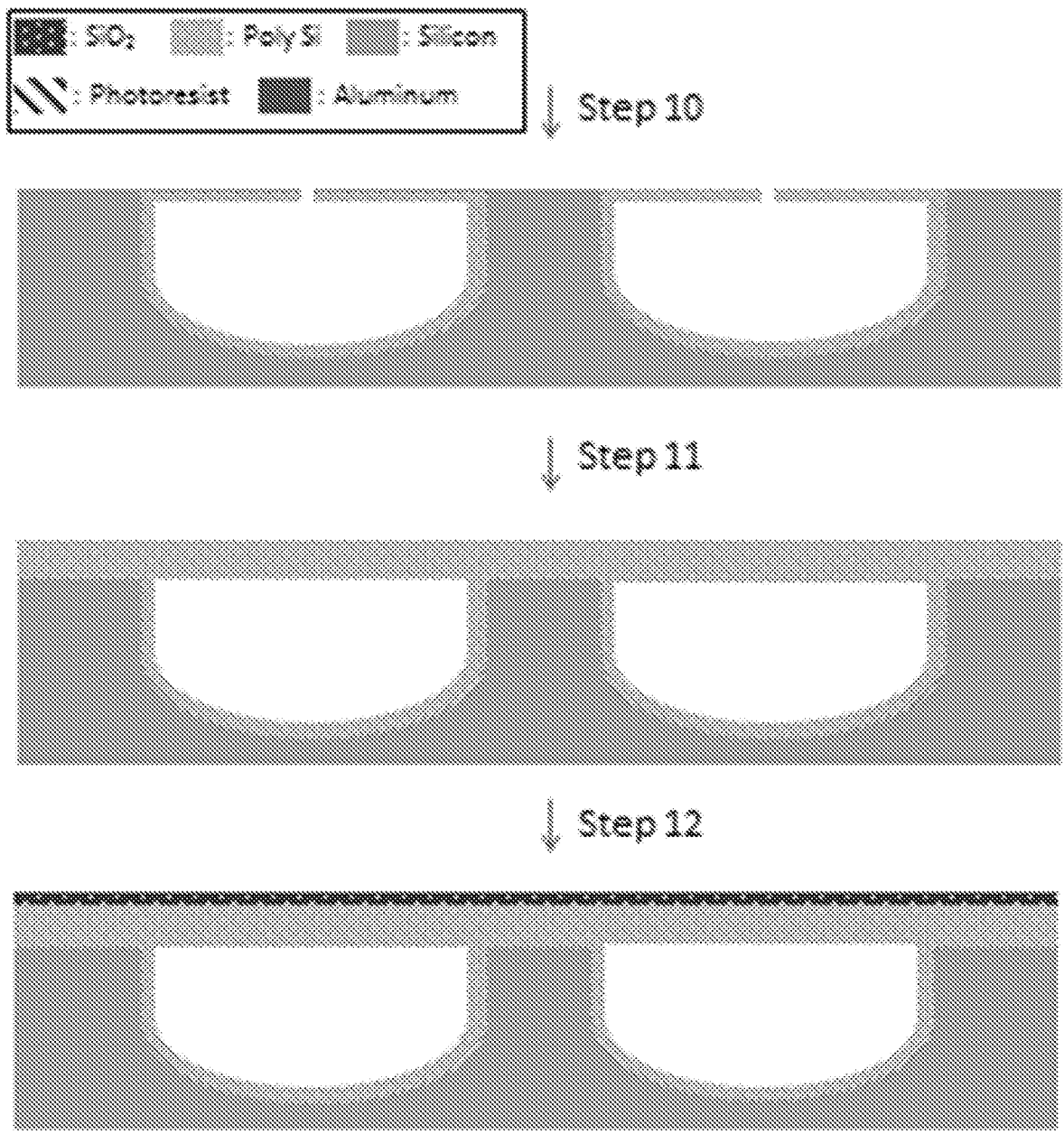
Figure 6:
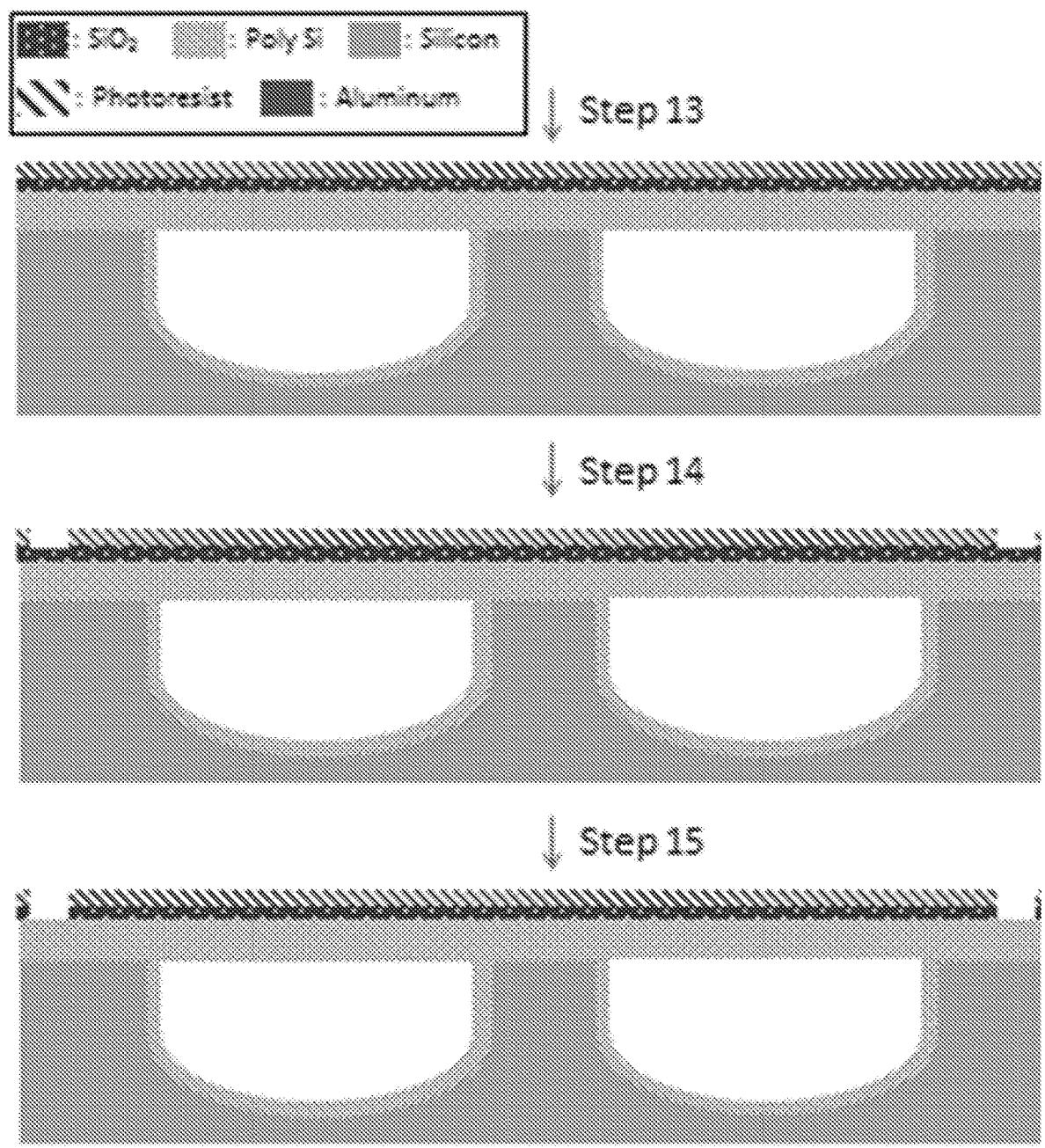
Figure 7:
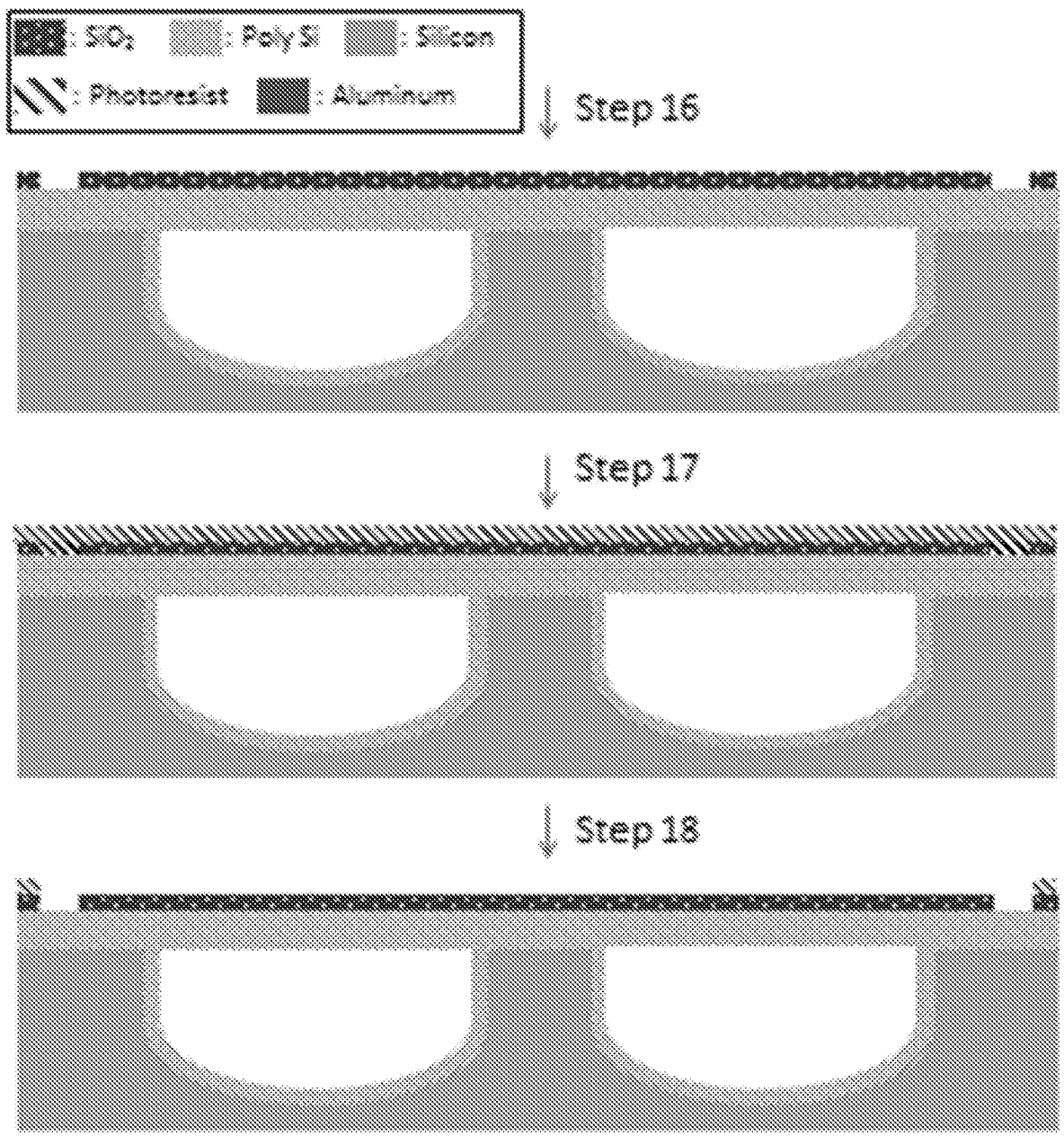
Figure 8:
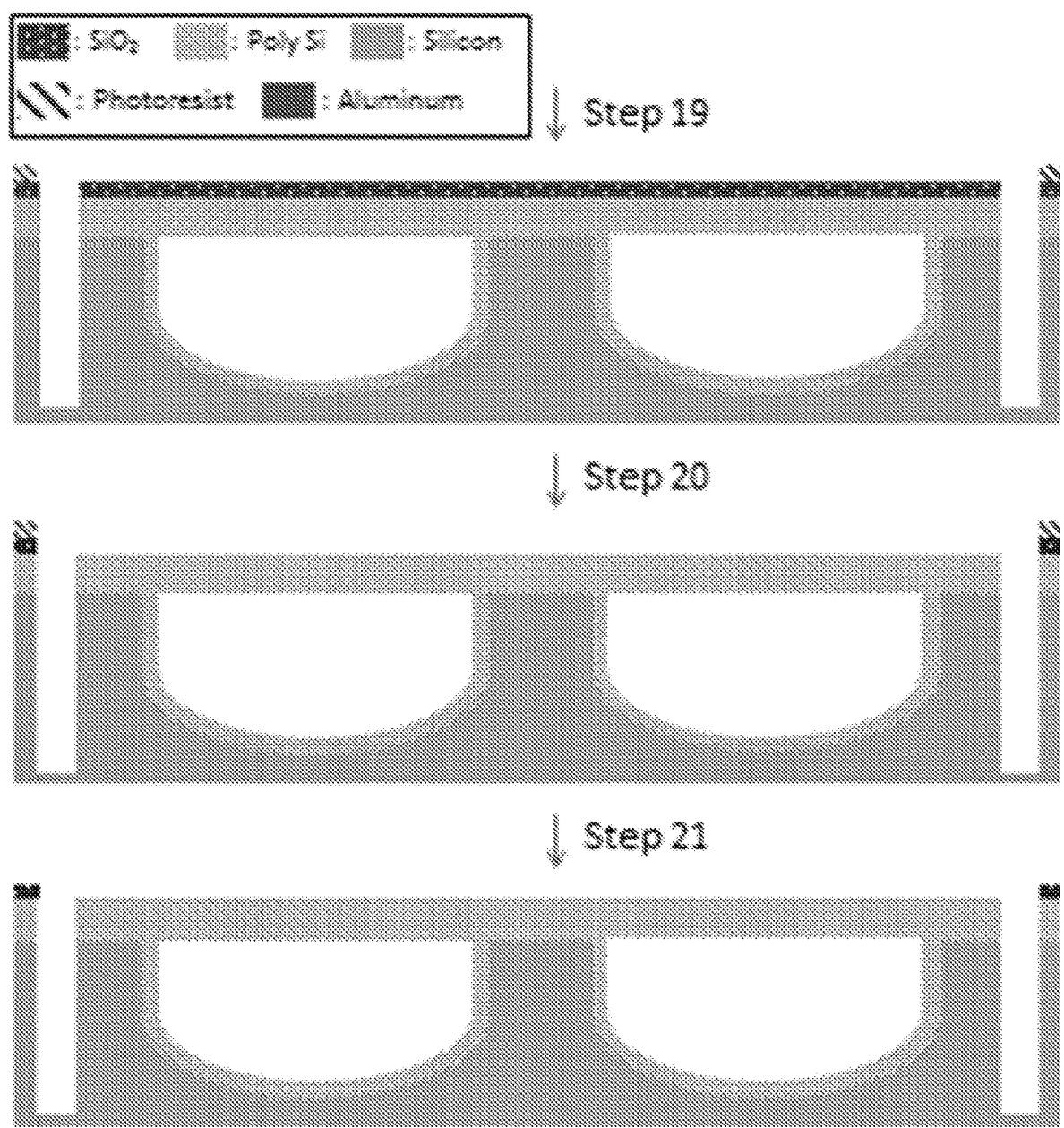

Probes were fabricated on 4 inch p-type wafers (Silicon Valley Microelectronics, Santa Clara, Calif.) using the process outlined in FIG. 2. A 2 μm silicon dioxide layer was grown on a wafer by wet oxidation using a Tempress TS 6604 S3 tool (FIG. 2). The initial line for channel etching was patterned by lithography in 3 μm of SPR220 photoresist (Dow, Marlborough, Mass.), see FIG. 2A. The exposed $SiO_2$ was removed with DRIE using the Bosch process (which uses $C_4F_8$ as a passivation material) with a STS Deep Silicon Etcher (FIG. 2A) and semicircular shaped channels (FIG. 2B) were formed using a SPTS Xactix $XeF_2$ etcher (Allentown, Pa.) (FIG. 3). Channels were sealed by chemical vapor deposition (Tempress TS 6604 S3/T3) of 3 μm of polysilicon. The polysilicon layer on the wafer surface was etched with DRIE until the buried $SiO_2$ layer was exposed and then removed by treatment with buffered hydrofluoric acid (Transene Co Inc, Danvers, Mass.) for 20 min (FIG. 4). An additional 2 μm polysilicon layer was deposited followed by the deposition of a 1 μm $SiO_2$ layer for recovery of potential damage during the polysilicon removal process (FIG. 5) The probe shape was patterned by a second lithography step and exposed $SiO_2$ was removed by DRIE. After photoresist removal in PRS 2000 (Avantor Performance Materials, Phillipsburgh, N.J.), a sampling area at the probe tip was patterned by a third lithography step. The outline of the probe was etched by DRIE to 150 μm depth and $SiO_2$ layer on the channel was removed in buffered hydrofluoric acid (FIGS. 6-8). Finally, polysilicon thickness on the sampling area was reduced to 2 μm by DRIE (FIG. 9, step 22).

Membrane Formation and Probe Release from Wafer.

Figure 9:
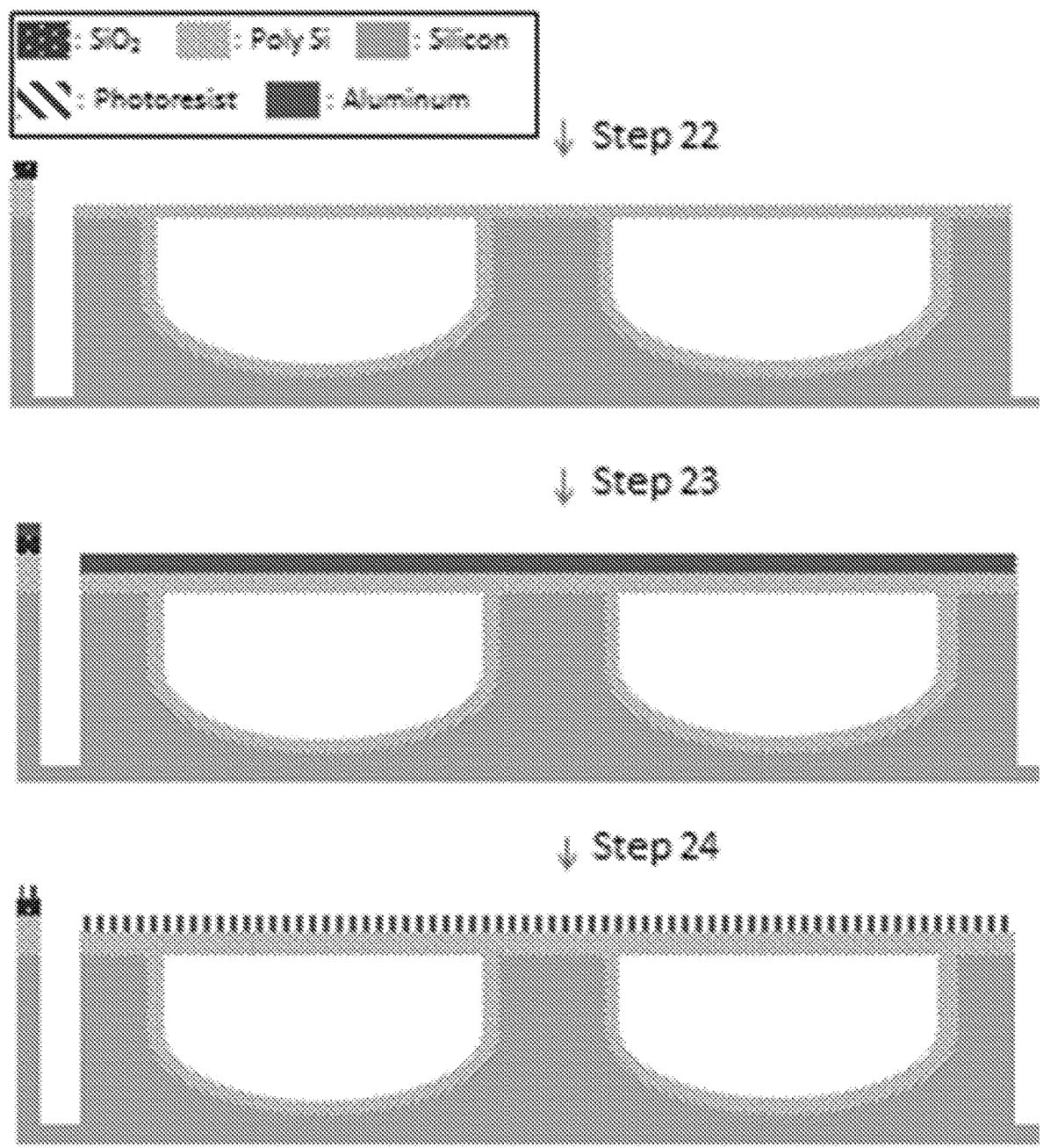

A 400 nm Al layer was deposited over the wafer using an e-beam evaporator (Denton Vacuum, Moorestown, N.J.), FIG. 2F (FIG. 9, step 23). The Al coating was anodized at 60 V and 15° C. in 0.3 M oxalic acid solution for 15 min using Pt mesh (Alfa Aesar, Ward Hill, Mass.) as a counter electrode (FIG. 9, step 24) (see also FIG. 16).

Figure 10:
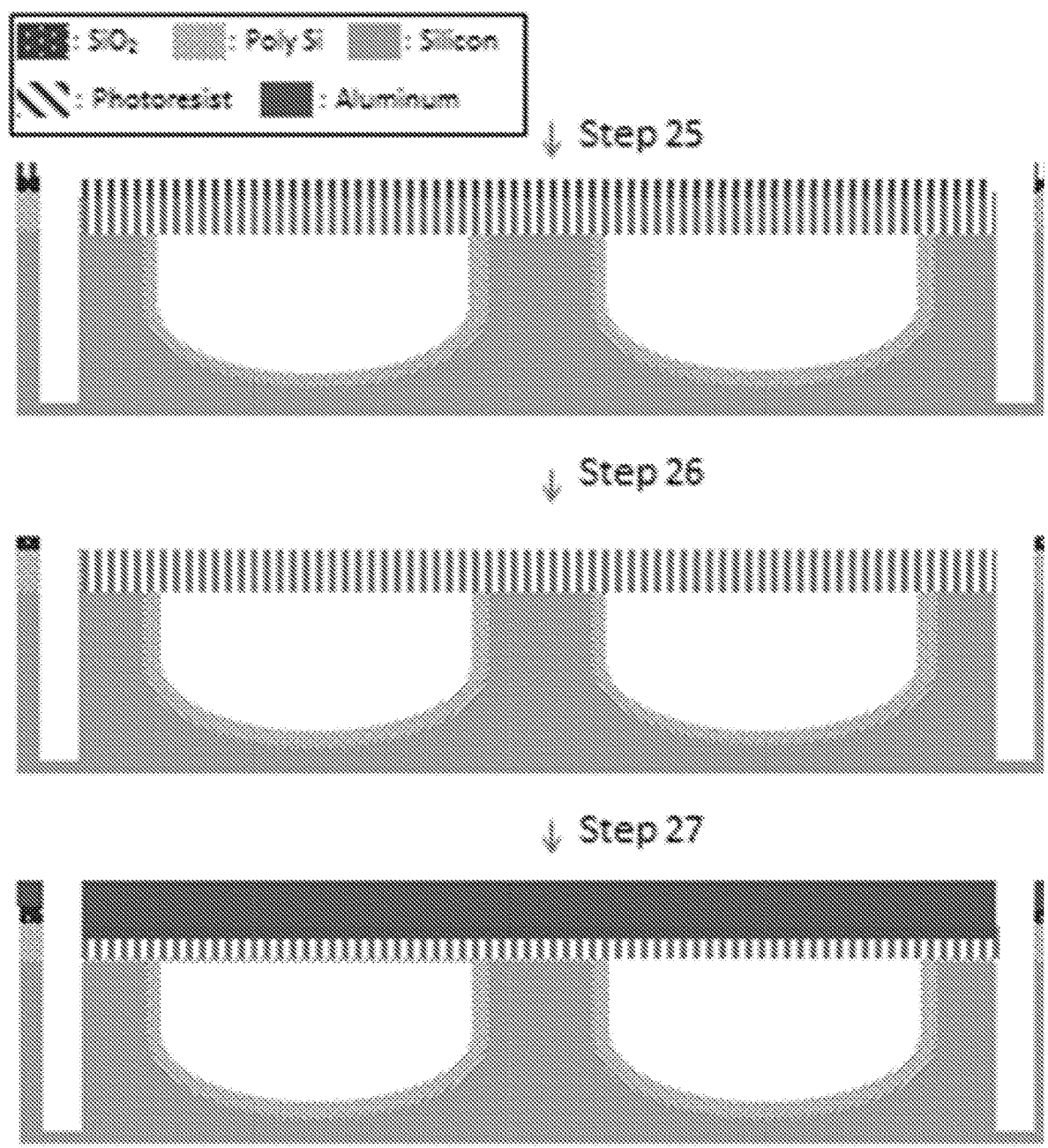
Figure 11:
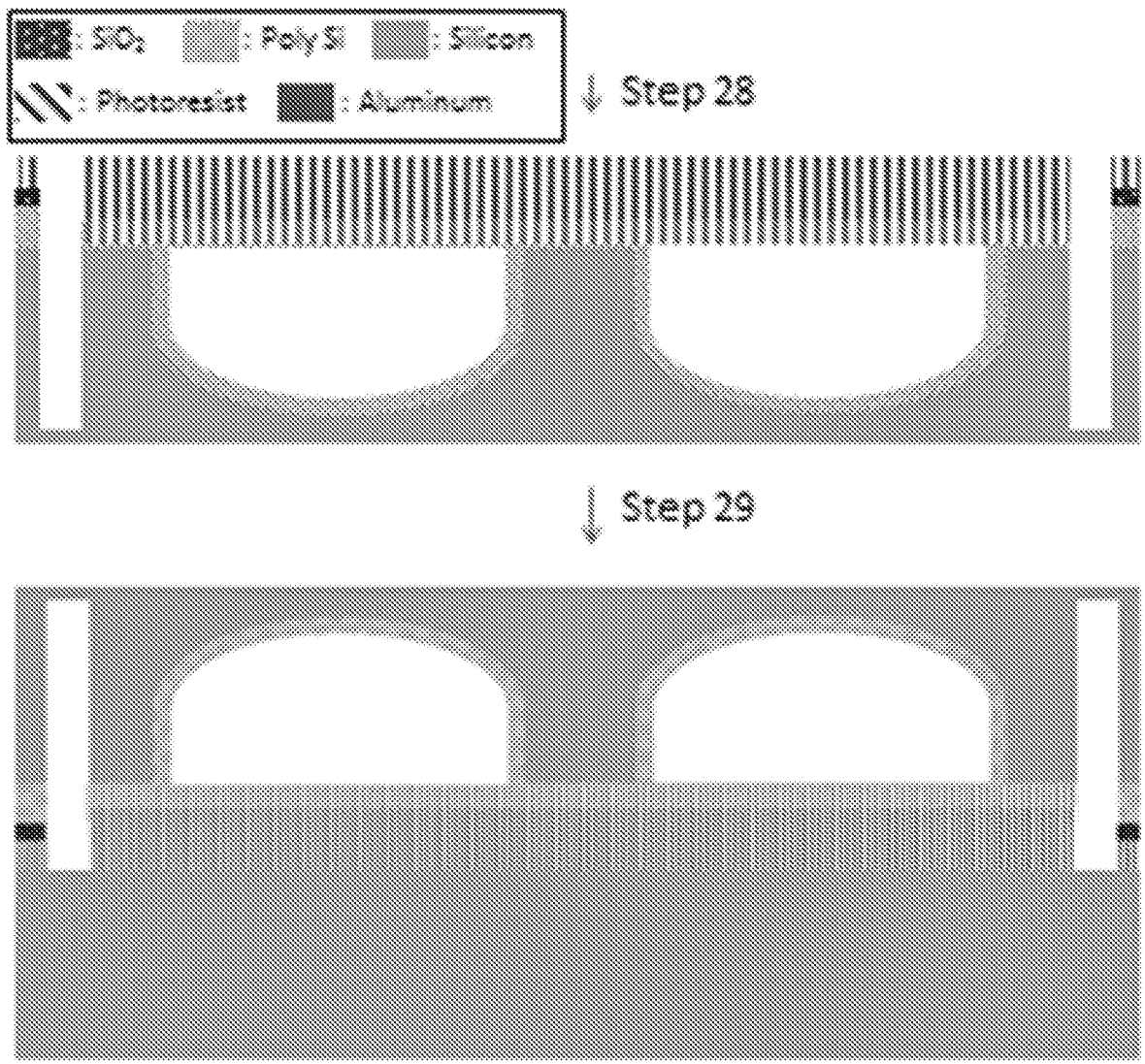
Figure 12:
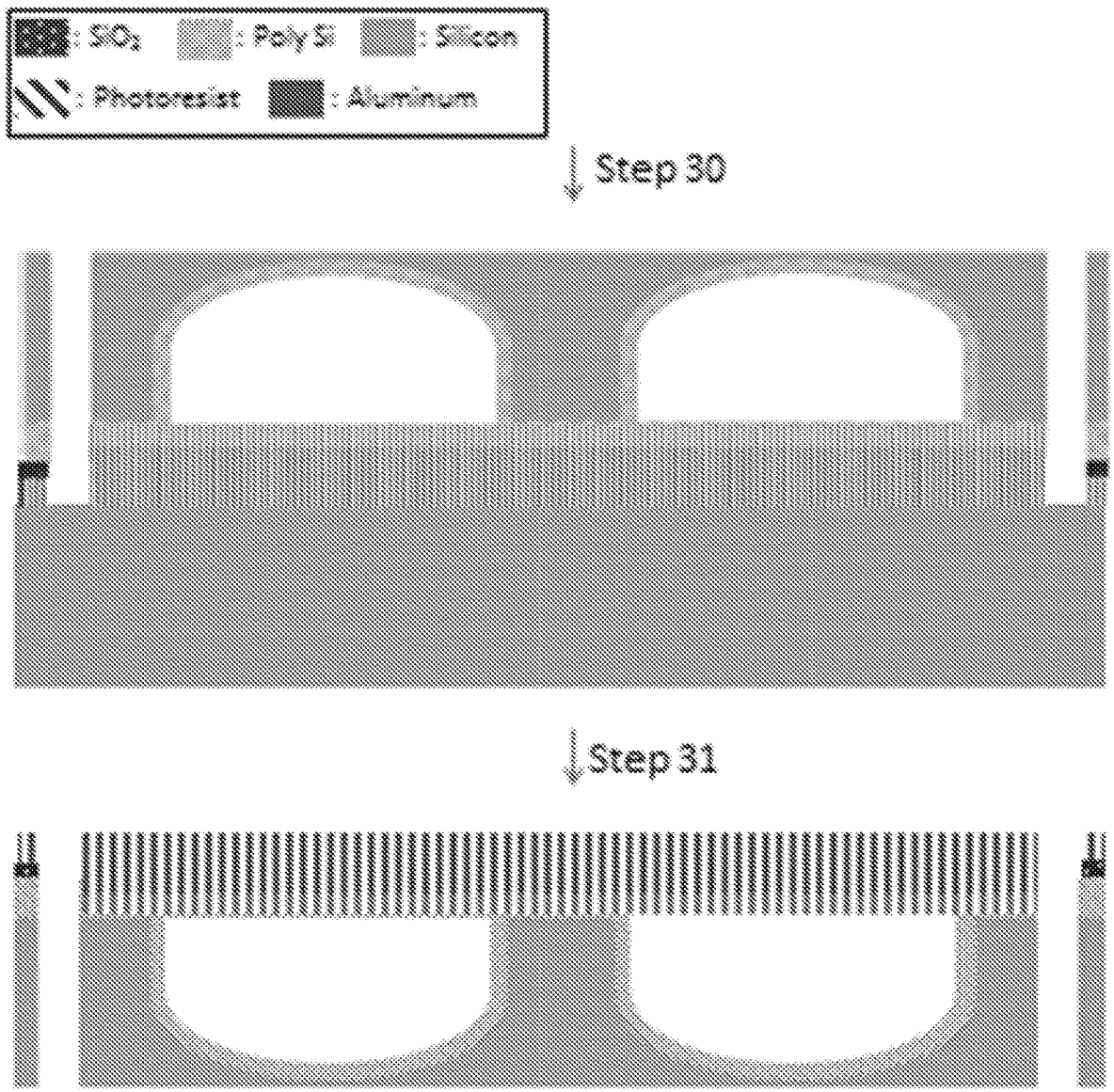

The wafer was rinsed with deionized water and then treated with 5% phosphoric acid at room temperature for 50 min to widen the pores (FIG. 9, step 24, pore widening is not shown as a separate step. The polysilicon layer overlying the microchannel was etched by DRIE at −15° C. using the AAO layer as a mask (FIG. 10, step 25). The AAO membrane was removed by treating with 5% phosphoric acid at 65° C. for 1 h (FIG. 10, step 26) A fresh 3 μm Al layer was deposited using the Enerjet evaporator (FIG. 10, step 27). (For this step, the wafer was tilted to a 45° angle in order to prevent blocking of previous etched holes on polysilicon layer by Al metal vapor.) The Al layer was anodized at 60 V and 15° C. in 0.3 M oxalic acid solution for 45 min and pores widened by treating with 5% phosphoric acid at room temperature for 90 min (FIG. 11, step 28). The results of each process were imaged by scanning electron microscopy (Hitachi SU8000 SEM). The wafer with embedded AAO membrane was bonded to a carrier wafer with Crystalbond 555 (Structure Probe, Inc., West Chester, Pa.) and backside etched by DRIE until the probe thickness reached 40 μm (FIG. 11, step 29). Individual probes were released in hot water.

Probe Holder Fabrication and Assembly

Resulting probes were too small and fragile to be conveniently handled and plumbed to connection tubing; therefore, a holder was microfabricated similar to that described previously for push-pull probes.[14] (See Lee, W. H.; Slaney, T. R.; Hower, R. W.; Kennedy, R. T. *Anal. Chem.* 2013, 85, 3828-3831, the full disclosure of which is hereby incorporated by reference). A non-limiting description of holder fabrication and assembly is given in FIG. 17. 12 cm lengths of 100 μm I.D.×360 μm O.D. capillary were connected to the inlet and outlet. The outlet capillary was then joined to a 22 cm long, 50 μm I.D.×360 μm O.D. fused-silica capillary for fraction collection. Flow through probes was driven using a Chemyx syringe pump (Stafford, Tex.).

In Vitro Characterization

To determine the dynamic response during sampling, probes were perfused with water at a flow rate of 100 nL/min and placed into a stirred vial of water (see FIG. 18A). The solution was subsequently changed to a 50 μM fluorescein solution while recording fluorescence within the exit tubing using a fluorescence microscope.

For study of probe relative recovery, the microfabricated probe ("μFab") was compared to a concentric microdialysis probe ("MD") which was prepared as previously described. The concentric probe had a regenerated cellulose membrane with 18 kDa molecular weight cut-off that was 4 mm long and 220 μm diameter (Spectrum Labs, Rancho Dominguez, Calif.). Probes were dipped into a well-stirred vial containing: 0.5 μM acetylcholine (ACh), dopamine (DA), 3-methoxytyramine (3-MT), and serotonin (5-HT); 1 μM 3,4-dihydroxyphenylalanine (DOPA) and histamine (Hist); 10 μM 3,4-dihydroxyphenylacetic acid (DOPAC), γ-aminobutyric acid (GABA), 5-hydroxyindoleacetic acid (5-HIAA), homovanillic acid (HVA), phenylalanine (Phe), and tyrosine (Tyr); 50 μM choline (Cho), serine (Ser), and taurine (Tau); and 1 mM glucose (Gluc) in aCSF at 37° C. The aCSF was supplemented with 0.25 mM ascorbate to protect against oxidation of analytes. After an equilibration time of 30 min, dialysates were collected in 20 min fractions with a perfusion rate of 100 nL/min.

Dialysate samples were derivatized with benzoyl chloride and analyzed by LC-MS, as described previously. Briefly, 1.5 μL of standards or fractions were mixed with 3 μL of 100 mM sodium carbonate buffer at pH 11 and 3 μL benzoyl chloride (2% in acetonitrile, v/v). The samples were mixed with 3 μL of [$^{13}$C]-labeled or [d4]-labeled benzoylated internal standards, consisting of 5 nM [$^{13}$C]-DA, [$^{13}$C]-3-MT, [$^{13}$C]-5-HT, and [$^{13}$C]-DOPA; 10 nM [d4]-ACh and [d4]-Cho; 50 nM [$^{13}$C]-GABA and [$^{13}$C]-Hist; 125 nM [$^{13}$C]-DOPAC, [$^{13}$C]-5-HIAA, and [$^{13}$C]-Tyr; 0.5 μM [$^{13}$C]-Tau ad Gln; 1.25 μM [$^{13}$C]-Phe and [$^{13}$C]-Ser; and 12.5 μM [$^{13}$C]-Gluc in 50% acetonitrile v/v containing 1% sulfuric acid. Samples were analyzed using an Accela UHPLC interfaced to a TSQ Quantum Ultra triple quadrupole mass spectrometer (Thermo Fisher Waltham, Mass.) operated in multiple reaction monitoring mode. 3 μL samples were injected onto a 2.1 mm×100 mm Phenomenex biphenyl Kinetex HPLC column (Torrance, Calif.). Mobile phase A was 10 mM ammonium formate with 0.15% formic acid, and mobile phase B was acetonitrile. The mobile phase gradient was: initial, 0% B; 0.01 min, 19% B; 1 min, 26% B; 1.5 min, 75% B; 2.5 min, 100% B; 3 min, 100% B; 3.1 min, 5% B; and 3.5 min, 5% B at 0.45 mL/min.

In Vivo Sampling

All procedures were conducted according to a protocol approved by the University Committee for the Use and Care of Animals (UCUCA). Male Sprague-Dawley rats weighing between 250-300 g, (Harlan, Indianapolis, Ind., USA) were used for all experiments. Rats were housed in a temperature and humidity controlled room with 12 h light/dark cycles with access to food and water ad libitum. Measures were taken to prevent animal pain and discomfort throughout the experiment. All animal experiments were within the guidelines of Animal Research Reporting in vivo Experiments (ARRIVE).

Animals were anesthetized using 2-4% isoflurane and placed in a stereotaxic frame (David Kopf, Tujunga, Calif.). Two burr holes were drilled above the striatum +1.0 mm anterior-posterior and ±3.0 mm lateral from bregma. The MD probe and µFab probe were lowered into opposite hemispheres −6.15 mm from the top of the skull. Rats were maintained under anesthesia for the duration of the experiment using isoflurane. Both probes were perfused with aCSF at 100 nL/min. After 1 h equilibration, two 20 min fractions were collected for basal concentrations (2 µL per fraction) and two more were collected after an amphetamine injection (5 mg/kg, i.p). Following the experiment, the probes were withdrawn from the brain using the stereotaxic frame and the rat was euthanized. Brains were extracted to confirm probe placement.

Results and Discussion
Probes

Figure 13:
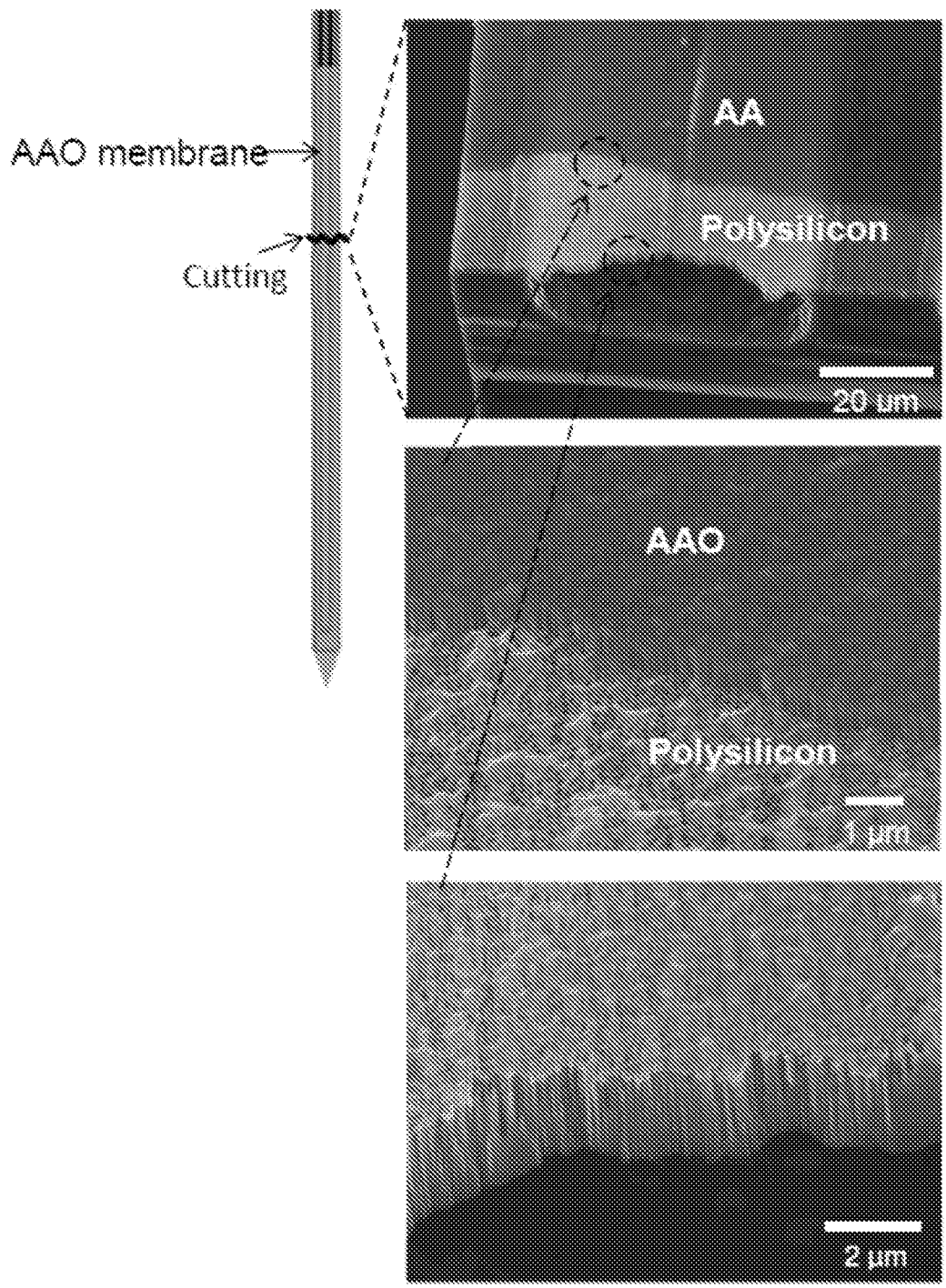
FIG. 13 gives SEM images of fabricated microchannels with uniform parallel pores. Drawing at left indicates where the probe sampling tip was broken to expose channels. Images show AAO and polysilicon membranes overlaid. Lowest image shows that pores go through the polysilicon base layer over the open channel. Images correspond to probe at about step 25 shown in FIG. 10.

A challenge in fabricating microdialysis probes is embedding nanoporous membranes over channels while balancing the need for sufficient physical strength and good recovery across the membrane. The process described in FIGS. 2 to 12 allowed formation of a nanoporous membrane covering a total of 8 mm length of channel (but only 4 mm length of probe because the channel has a 180° turn at the tip). The resulting 5 µm thick membrane has straight pores that are 60-80 nm wide at a density of $8.4 \times 10^{13}/m^2$ (FIG. 13). 50-70 probes (representing a 50% success rate) could be recovered from a single wafer. AAO membranes have been previously used as a photomask on a solid surface;[31] but with these teachings, AAO is used as a DRIE mask directly over a microchannel.

In preliminary experiments fabrication stopped at Step 25 in FIG. 10 and continued at step 29 (FIG. 11); however, we found that the resulting membranes were fragile and ruptured when attempting to flow through the probe. The additional 3 µm AAO membrane (FIG. 10, step 27)) gave the probes sufficient mechanical strength. A potential drawback of this approach is that the final AAO pores would not necessarily line up exactly with the polysilicon pores; however, it was discovered that the pore density was nevertheless sufficient to provide enough overlap and allow molecular exchange as described below.

In Vitro Characterization

The response of the µFab probe to a change in concentration was determined by switching the sampled solution from 0 µM to 50 µM fluorescein while monitoring fluorescence at the probe outlet (see FIG. 18). Fluorescence signals began to increase 14.5 min after switching. This delay is expected because the perfusion rate was 100 nL/min and the internal volume from sampling tip to detection point was ~1400 nL. The good agreement shows that leakage through the system was insignificant and allows accurate correlation of concentration changes in collected fractions and time of event in the sample. Once the fluorescence signal increased, it had a 10-90% rise time of 47±2 s (n=7). This rise time, which determines the best possible temporal resolution, is close to the estimated rise time of 44 s using the combined diffusion and Taylor dispersion equation.[32] The predicted rise time is 1 s for probe channel and 43 s for combined outlet and collection capillaries. Because most of the dispersion is in the connecting channel, it may be possible to improve temporal resolution by using segmented flow or smaller connection capillaries.[32-34]

In vitro relative recovery of neurochemicals was evaluated by comparing dialysate samples with samples taken directly from the stirred vial (Table 1). For the µFab probe, the recovery was from 2 to 7% for selected neurochemicals. The variation in recovery may be caused by differences in molecular structure, charge effects, hydrophobicity, and membrane specificity. These results can be contrasted with the nearly 100% relative recovery obtained using the traditional probe at 100 nL/min. Compared to the MD probe, the µFab probe provides lower relative recovery values, at least in part, because of its 6-fold smaller surface area of sampling.

Table 1 shows in vitro recovery of selected neurochemicals at flow rate of 0.1 µL/min. The results from the microfabricated probes are compared with the conventional dialysis probes. Recovery values are given as mean±relative standard deviation (n=4 probes, 20 samples).

TABLE 1

| Analyte (tested concentration) | Recovery, % | RSD (%) | Recovery, % | RSD (%) |
|---|---|---|---|---|
| Acetylcholine (500 nM) | 7 | 24 | 105 | 9 |
| Choline (50 µM) | 6 | 25 | 99 | 16 |
| 3,4-Dihydroxyphenylacetic acid (10 µM) | 2 | 30 | 93 | 11 |
| 3,4-Dihydroxyphenylalanine (1 µM) | 3 | 17 | 95 | 12 |
| Dopamine (500 nM) | 5 | 18 | 100 | 7 |
| γ-Aminobutyric acid (10 µM) | 3 | 40 | 109 | 8 |
| Glucose (1 mM) | 3 | 23 | 97 | 12 |
| Glutamine (500 µM) | 2 | 45 | 104 | 10 |
| Histamine (1 µM) | 5 | 24 | 108 | 9 |
| 5-Hydroxyindoleacetic acid (10 µM) | 5 | 26 | 100 | 10 |
| Homovanillic acid (10 µM) | 3 | 40 | 105 | 10 |
| 3-Methoxytyramine (500 nM) | 4 | 25 | 95 | 13 |
| Phenylalanine (10 µM) | 4 | 50 | 119 | 12 |
| Serine (50 µM) | 3 | 33 | 112 | 18 |
| Serotonin (500 nM) | 4 | 20 | 103 | 7 |
| Taurine (50 µM) | 4 | 30 | 110 | 8 |
| Tyrosine (10 µM) | 4 | 33 | 105 | 11 |

To gain more insight into the recovery, computational modeling and simulation of fluid flowing through the µFab probe was performed (see FIG. 19). Initial modeling and simulation indicated that flow rate and porosity are main variables that significantly affect recovery. Using the diffusion coefficient for dopamine, estimated porosity of 33% and flow rate of 100 nL/min (FIG. 19A), the simulated recovery was 98%, much larger than our observed value of 5-7% for dopamine. When porosity was lowered to 1%, the simulated and actual recovery matched (FIG. 19B). These results suggest that porosity is lower than expected. This discrepancy may be due to several factors. The final overlaid AAO pores do not line up with the polysilicon pores resulting in lower porosity than measured by observing the top of the membrane surface. Some pores may also be clogged, e.g., with wax (used for wafer-mounting) during back-side etching. Changes in probe processing or modifying surfaces may prove useful to improve recovery.[35,36]

In Vivo Sampling

To determine their suitability for in vivo experiments, µFab probes were used to sample from the striatum of anesthetized rats. 13 neurochemicals were consistently detected in 20 min fractions with good signal to noise ratio (FIG. 14B). For comparison, we also sampled from the same animals with a MD probe operated at the same flow rate.

Basal concentrations from both types of probes are reported in Table 2. Concentrations were not corrected for recovery; however, the MD probes achieved nearly 100% recovery and therefore these concentrations can be considered a good estimate of the in vivo concentration[11]. Comparison of these concentrations with other reports of calibrated in vivo MD experiments reveals reasonable agreement for most neurochemicals.[34,37-43] Acetylcholine and dopamine are generally found in low nanomolar concentrations. Phenylalanine, 5-HIAA, and tyrosine are typically in low micromolar range (<10 μM) while glutamine, serine and taurine are in high micromolar range (>10 μM). We observed about 5 times higher concentration of glucose than prior reports; however, our experiment was performed with anesthetized rats which may account for this difference.

Comparison basal extracellular concentration by the microfabricated probes, conventional probes with previous reports. The in vivo recovery for the microfabricated probes is estimated by finding the ratio between [μFab] and [MD]. All measurements are from sampling of the striatum of rats. Values given as mean+SEM (n=10 samples from 5 animals). In vivo recovery of μFab probe estimated by dividing μFab concentration by MD concentration, where recovery was estimated at 100%.

or to artifacts that result from different tissue reactions due to membrane material and probe size.

To assess the probe performance in response to dynamic in vivo chemical changes, the μFab and MD probes were simultaneously used to monitor concentration changes of DA and other neurochemicals after AMPH administration. When expressing the changes as a percent of baseline, nearly identical changes are seen at both the MD and μFab probes as shown in FIG. 5. The large change of about 4300% for DA is in agreement with expected effect of AMPH which inhibits uptake and promotes secretion of DA.[46] Other measured neurochemicals that have significant changes ($p<0.05$, Student's t-test) in their post drug levels were DOPAC, DOPA, HVA, 5-HIAA, and Tyr. The overall results show the μFab probe provides dynamic measurements nearly the same to a MD probe under the conditions of 100 nL/min flow rate and 20 min fractions.

Histological examination of the sampling sites from both types of probes were performed to visualize overall probe placement within the brain (see FIG. 20). The μFab probe generates a much smaller tract than the MD probe as expected. This difference presumably results in lower tissue damage.

TABLE 2

| Analyte | Previously-reported concentration, μM (Anesthesia, Quantification method, Ref#) | Dialysate concentration, μM [MD] | [μfab] | Estimated in vivo recovery, % |
|---|---|---|---|---|
| ACh | 0.01 ± 0.003 (Ketamine, 20% in vitro recovery, 34) | 0.032 ± 0.0045 | 0.0045 ± 0.00046 | 14 ± 0.4 |
| Choline | | 11 ± 0.93 | 0.54 ± 0.022 | 5 ± 0.2 |
| DOPAC | 17.4 ± 2.6 (Awake, No-net-flux, 37) | 8.9 ± 1.4 | 0.74 ± 0.084 | 8 ± 0.8 |
| DOPA | | 0.15 ± 0.017 | 0.0056 ± 0.00041 | 4 ± 0.3 |
| Dopamine | 0.010 ± 0.0017 (Awake, No-net-flux, 37) | 0.0067 ± 0.00062 | 0.00032 ± 0.000046 | 5 ± 0.3 |
| Glucose | 350 ± 20 (Awake, No-net-flux, 40) | 1431 ± 82 | 56 ± 3.3 | 4 ± 0.2 |
| GABA | 0.12 ± 0.05 (Urethane, 20% in vitro recovery, 38) | 0.78 ± 0.34 | n.d. | — |
| Glutamine | 385 ± 16 (Awake, No-net-flux, 42) | 472 ± 24 | 18 ± 2.2 | 4 ± 0.3 |
| Histamine | | 0.039 ± 0.016 | n.d. | — |
| 5-HIAA | 3.5 ± 0.1 (Awake, Low-flow-rate, 37) | 1.2 ± 0.13 | 0.095 ± 0.016 | 8 ± 1.2 |
| HVA | 17 ± 1.1 (Awake, Low-flow-rate, 37) | 8.3 ± 1.1 | 0.81 ± 0.097 | 10 ± 0.9 |
| 3-MT | | 0.0069 ± 0.00046 | n.d. | — |
| Phe | 2 ± 0.2 (Chloral Hydrate, Low-flow-rate, 39) | 7.5 ± 0.49 | 0.22 ± 0.012 | 3 ± 0.1 |
| Serine | 7 ± 0.5 (Awake, Corrected for in vitro recovery, 41) | 36 ± 2.3 | 1.8 ± 0.12 | 5 ± 0.2 |
| 5-HT | | 0.019 ± 0.0042 | n.d. | — |
| Taurine | 25 ± 5.1 (Halothane, No-net-flux, 43) | 60 ± 4.9 | 2.8 ± 0.21 | 4 ± 0.1 |
| Tyrosine | 3.3 ± 0.9 (Chloral Hydrate, Low-flow-rate, 39) | 6.7 ± 0.33 | 0.22 ± 0.0011 | 3 ± 0.1 |

Figure 14:
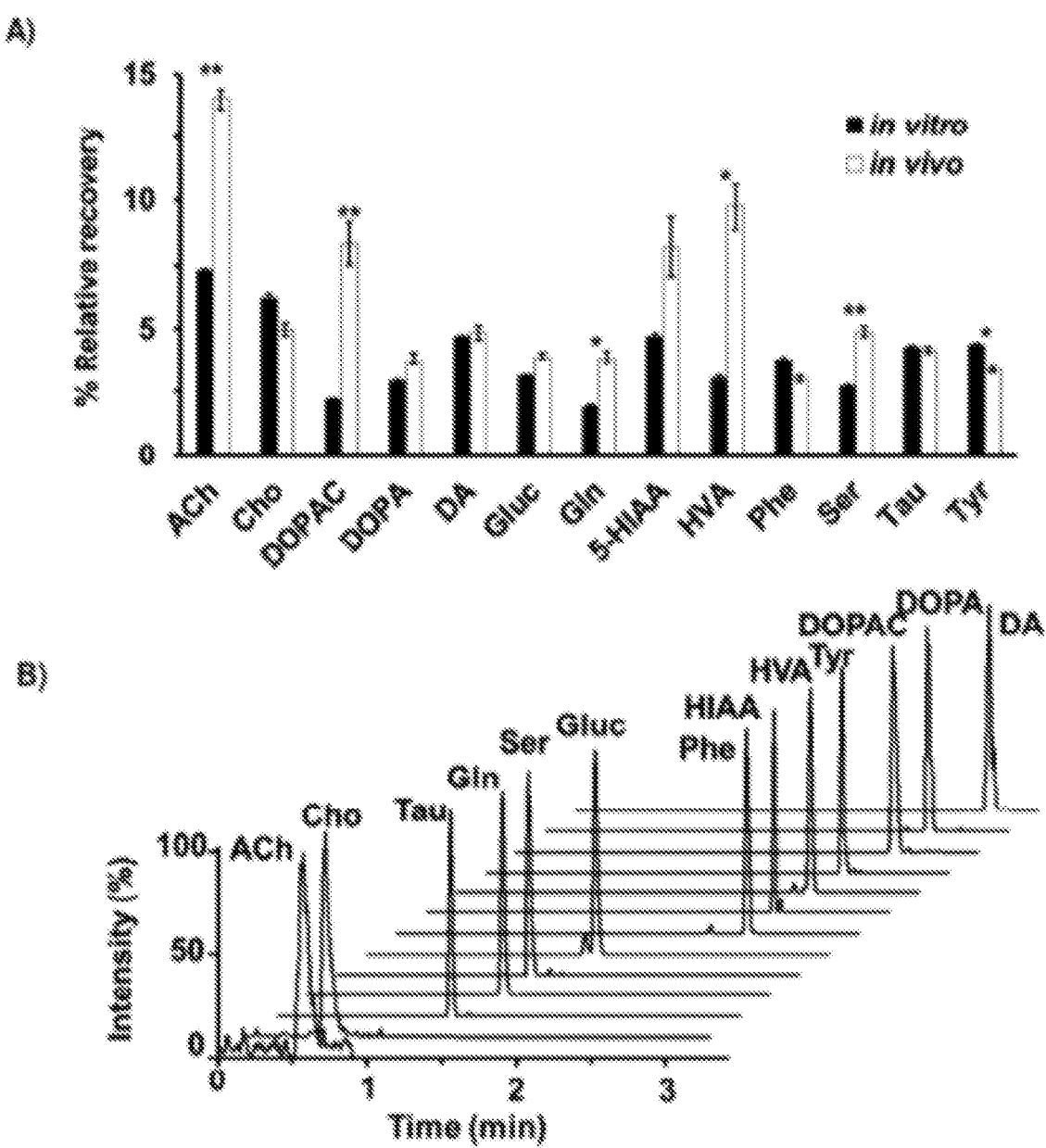
FIG. 14 shows (A) Comparison of relative recoveries of analytes between in vitro and in vivo experiments. The bar chart represents averaged relative recovery with standard error of the mean. * indicates different with $p<0.05$, ** indicates p<0.001 obtained by the two-tailed Student's t-test test. (B) Multiple reaction monitoring mass chromatograms of a representative fraction (1.5 μL) collected from the striatum of an anesthetized rat through the microfabricated probe. The chromatogram shows the trace for 13 detectable neurochemicals. Abbreviations used are: acetylcholine (ACh), choline (Cho), taurine (Tau), glutamine (Gln), serine (Ser), glucose (Gluc), phenylalanine (Phe), 5-hydroxyindoleacetic acid (5-HIAA), homovanillic acid (HVA), tyrosine (Tyr), 3,4-dihydroxyphenylacetic acid (DOPAC), 3,4-dihydroxyphenylalanine (DOPA), and dopamine (DA).

Because the MD probe recovery approaches 100% at 100 nL/min, the in vivo recovery of μFab probe could be estimated by dividing dialysate concentrations from μFab probes by dialysate concentrations from MD probes. This calculation assumes that the in vivo concentration is the same on both sides of the brain and at both probes. As shown in FIG. 14, the in vitro recovery and estimated in vivo recovery of the μFab probe are comparable for 7 of the neurochemicals. For several compounds (Gln, HVA, Tyr, Ach, DOPAC, and Ser) the estimated in vivo recovery is significantly higher than in vitro recovery. The origin for this difference is not clear. It is possible that active processes and mass transport within the brain is sufficiently different from in vitro for these analytes to cause the in vitro recovery to differ from the in vivo recovery.[44,45] Another interpretation is that the actual basal concentrations from the sampling site of μFab probe are higher than the concentrations from MD probe sampling. Such discrepancies could be due to differences in local concentrations (different areas were sampled)

CONCLUSIONS

The in vivo results show that the μFab probe can be reliably used for studying neurochemicals and monitoring dynamic chemical changes in live animal brain. The chief advantage of the probes is that they have 79% smaller cross-section than conventional MD probes and therefore can be used in smaller subjects and brain regions. The low recovery at 100 nL/min is a drawback of these probes; however, preliminary experiments suggest that small changes membrane fabrication will mitigate this issue. Fortunately, the excellent sensitivity of LC-MS allows many neurochemicals to be detected even at this recovery. A likely route to improve temporal resolution and detect less abundant analytes is to use miniaturized analytical methods like capillary LC, CE, or droplet enzyme assays.[32,47-51] The sensitivity of such methods would allow good temporal resolution while preserving the advantages of better spatial resolution and lower tissue damage. The use of microfabricated probes may allow integration of other functionality such as electrodes for chemical or potential sensing, microfluidics for sample preparation (e.g., derivatization), or droplet formation for fraction collection at nanoliter scale. The probe may also be utilized for other applications that require continuous chemical sampling or delivery from microenvironments.

REFERENCES (1) Darvesh, A. S.; Carroll, R. T.; Geldenhuys, W. J.; Gudelsky, G. A.; Klein, J.; Meshul, C. K.; Van der Schyf, C. J. *Exp. Op. Drug Disc.* 2011, 6, 109-127.
(2) Watson, C. J.; Venton, B. J.; Kennedy, R. T. *Anal. Chem.* 2006, 78, 1391-1399.
(3) Yang, C.-S.; Tsai, P.-J.; Chen, W.-Y.; Liu, L.; Kuo, J.-S. *J. Chromatogr. B* 1995, 667, 41-48.
(4) Bungay, P. M.; Newton-Vinson, P.; Isele, W.; Garris, P. A.; Justice, J. B. *J. Neurochem.* 2003, 86, 932-946.
(5) Zahn, J. D.; Trebotich, D.; Liepmann, D. *Biomed. Microdevices* 2005, 7, 59-69.
(6) Chen, X.; Prow, T. W.; Crichton, M. L.; Jenkins, D. W.; Roberts, M. S.; Frazer, I. H.; Fernando, G. J.; Kendall, M. A. *J. Control. Release* 2009, 139, 212-220.
(7) Lee, H. J.; Son, Y.; Kim, D.; Kim, Y. K.; Choi, N.; Yoon, E.-S.; Cho, I.-J. *Sens. Actuator B-Chem.* 2015, 209, 413-422.
(8) Chandrasekaran, S.; Brazzle, J. D.; Frazier, A. B. *J. Microelectromech. Syst.* 2003, 12, 281-288.
(9) Lee, J. W.; Park, J.-H.; Prausnitz, M. R. *Biomaterials* 2008, 29, 2113-2124.
(10) Verhoeven, M.; Bystrova, S.; Winnubst, L.; Qureshi, H.; De Gruijl, T. D.; Scheper, R. J.; Luttge, R. *Microelectron. Eng.* 2012, 98, 659-662.
(11) Jina, A.; Tierney, M. J.; Tamada, J. A.; McGill, S.; Desai, S.; Chua, B.; Chang, A.; Christiansen, M. *J. Diabetes Sci. Technol.* 2014, 8, 483-487.
(12) Ainla, A.; Jeffries, G. D.; Brune, R.; Orwar, O.; Jesorka, A. *Lab Chip* 2012, 12, 1255-1261.
(13) Li, C. G.; Lee, C. Y.; Lee, K.; Jung, H. *Biomed. Microdevices* 2013, 15, 17-25.
(14) Lee, W. H.; Slaney, T. R.; Hower, R. W.; Kennedy, R. T. *Anal. Chem.* 2013, 85, 3828-3831.
(15) Kotake, N.; Suzuki, T.; Mabuchi, K.; Takeuchi, S. *Int. Conf. Miniaturized Syst. Chem. Life Sci.*, 12th 2008, 1687-1689.
(16) Metz, S.; Trautmann, C.; Bertsch, A.; Renaud, P. In *IEEE Int. Conf. Micro Electro Mech. Syst.*, 15th; IEEE, 2002, 81-84.
(17) Desai, T. A.; Hansford, D.; Ferrari, M. *J. Membr. Sci.* 1999, 159, 221-231.
(18) Lebouitz, K. S.; Mazaheri, A.; Howe, R.; Pisano, A. In *IEEE Int. Conf. Micro Electro Mech. Syst.*, 12th; IEEE, 1999, 470-475.
(19) Chung, H. H.; Chan, C. K.; Khire, T. S.; Marsh, G. A.; Clark, A.; Waugh, R. E.; McGrath, J. L. *Lab Chip* 2014, 14, 2456-2468.
(20) Leïchlé, T.; Bourrier, D. *Lab Chip* 2014.
(21) Striemer, C. C.; Gaborski, T. R.; McGrath, J. L.; Fauchet, P. M. *Nature* 2007, 445, 749-753.
(22) Song, S.; Singh, A. K.; Shepodd, T. J.; Kirby, B. *J. Anal. Chem.* 2004, 76, 2367-2373.
(23) Song, S.; Singh, A. K.; Kirby, B. *J. Anal. Chem.* 2004, 76, 4589-4592.
(24) Hsieh, Y.-C.; Zahn, J. D. *J. Diabetes Sci. Technol.* 2007, 1, 375-383.
(25) Trautmann, C.; Brüchle, W.; Spohr, R.; Vetter, J.; Angert, N. *Nucl. Instrum. Methods Phys. Res., Sect. B* 1996, 111, 70-74.
(26) Poinern, G. E. J.; Ali, N.; Fawcett, D. *Materials* 2011, 4, 487-526.
(27) Suh, J. S.; Lee, J. S. *Appl. Phys. Lett.* 1999, 75, 2047-2049.
(28) Diggle, J. W.; Downie, T. C.; Goulding, C. *Chem. Rev.* 1969, 69, 365-405.
(29) Church, W. H.; Justice Jr, J. B. *Anal. Chem.* 1987, 59, 712-716.
(30) Song, P.; Mabrouk, O. S.; Hershey, N. D.; Kennedy, R. T. *Anal. Chem.* 2012, 84, 412-419.
(31) Wu, S.; Bammatter, M.-O.; Tang, W.; Auzelyte, V.; Zhang, H.; Brugger, J. In *IEEE Int. Conf. Nano/Micro Eng. Mol. Syst.*, 8th; IEEE, 2013, 986-989.
(32) Slaney, T. R.; Nie, J.; Hershey, N. D.; Thwar, P. K.; Linderman, J.; Burns, M. A.; Kennedy, R. T. *Anal. Chem.* 2011, 83, 5207-5213.
(33) Wang, M.; Slaney, T.; Mabrouk, O.; Kennedy, R. T. *J. Neurosci. Methods* 2010, 190, 39-48.
(34) Song, P.; Hershey, N. D.; Mabrouk, O. S.; Slaney, T. R.; Kennedy, R. T. *Anal. Chem.* 2012, 84, 4659-4664.
(35) Popat, K. C.; Mor, G.; Grimes, C. A.; Desai, T. A. *Langmuir* 2004, 20, 8035-8041.
(36) Feichtner, F.; Schaupp, L.; Koehler, H. *Devices for and methods of monitoring a parameter of a fluidic sample by microdialysis*; U.S. Pat. No. 8,535,537, Sep. 17, 2013.
(37) Smith, A. D.; Olson, R. J.; Justice, J. J. B. *J. Neurosci. Methods* 1992, 44, 33-41.
(38) Herrera-Marschitz, M.; You, Z. B.; Goiny, M.; Meana, J. J.; Silveira, R.; Godukhin, O. V.; Chen, Y.; Espinoza, S.; Pettersson, E.; Loidl, C. F.; others. *J. Neurochem.* 1996, 66, 1726-1735.
(39) Lada, M. W.; Kennedy, R. T. *Anal. Chem.* 1996, 68, 2790-2797.
(40) Fray, A. E.; Boutelle, M.; Fillenz, M. *J. Physiol.* 1997, 504, 721-726.
(41) Hashimoto, A.; Kanda, J.; Oka, T. *Brain Res. Bull.* 2000, 53, 347-351.
(42) Kanamori, K.; Ross, B. D. *J. Neurochem.* 2004, 90, 203-210.
(43) Molchanova, S.; Oja, S. S.; Saransaari, P. *Amino Acids* 2004, 27, 261-268.
(44) Benveniste, H.; Hüttemeier, P. C. *Prog. Neurobiol.* 1990, 35, 195-215.
(45) Menacherry, S.; Hubert, W.; Justice Jr, J. B. *Anal. Chem.* 1992, 64, 577-583.
(46) Butcher, S. P.; Fairbrother, I. S.; Kelly, J. S.; Arbuthnott, G. W. *J. Neurochem.* 1988, 50, 346-355.
(47) Tucci, S.; Rada, P.; Sepúlveda, M. J.; Hernandez, L. *J. Chromatogr. B* 1997, 694, 343-349.
(48) Boyd, B. W.; Witowski, S. R.; Kennedy, R. T. *Anal. Chem.* 2000, 72, 865-871.
(49) Song, H.; Chen, D. L.; Ismagilov, R. F. *Angew. Chem., Int. Ed.* 2006, 45, 7336-7356.
(50) Shackman, H. M.; Shou, M.; Cellar, N. A.; Watson, C. J.; Kennedy, R. T. *J. Neurosci. Methods* 2007, 159, 86-92.
(51) Wang, M.; Hershey, N. D.; Mabrouk, O. S.; Kennedy, R. T. *Anal. Bioanal. Chem.* 2011, 400, 2013-2023.

What is claimed is:

1. A microfabricated microdialysis probe made of a unitary block and comprising, from proximal to distal end, a body, a support shank, a shank, and a tip, wherein the body comprises an inlet port and an outlet port;
the probe further comprising a single channel in the surface of the probe and running from the inlet port to the shank, through the body, through the support shank, and through the shank to the tip and back to the outlet port, the inlet port and the outlet port both being on the proximal end,
wherein a porous layer covers the channel in at least part of the shank and a solid layer covers the channel everywhere the porous layer does not, wherein the porous layer has a plurality of pores having a diameter in the range of 50 nm to 100 nm.

2. The probe according to claim 1, wherein the channel path is straight with a U-shape turn at the tip.

3. The probe according to claim 1, wherein the tip is pointed to facilitate entry of the probe into a tissue.

4. The probe according to claim 1, wherein the overall length of the probe is 2 to 11 mm.

5. The probe according to claim 1, wherein the thickness of the shank is 10 to 40 microns and the other parts have the same thickness as or a greater thickness than the shank.

6. The probe according to claim 5, wherein the width of the shank is 30 to 180 microns.

7. The probe according to claim 1, wherein the depth of the channel is 5 to 35 microns and the width of the channel is 5 to 65 microns.

8. The probe according to claim 1, wherein the solid layer comprises polysilicon.

9. The probe according to claim 1, wherein the porous layer comprises anodized aluminum oxide.

10. The probe according to claim 1, wherein the porous layer comprises a polysilicon layer and a layer of anodized aluminum oxide, wherein the polysilicon layer covers the channel and is in contact with the unitary block and the anodized aluminum oxide layer is disposed on top of the polysilicon.

11. The probe according to claim 1, wherein the porous layer has a thickness of 1 to 10 microns.

12. The probe according to claim 1, wherein the porous layer covers a 0.1 to 8 mm length of the shank, including over a portion of the channel.

13. The probe according to claim 1, wherein the unitary block is made of silicon.

14. The probe according to claim 1, wherein the porous layer is characterized by a pore density of $8\pm2\times10^{13}$ per square meter.

15. The probe according to claim 1, wherein the porous layer is characterized by a porosity of 16 to 70 percent, where the porosity is defined as the ratio of the area of the pores to the area of the membrane.

16. A method of identifying molecules in a fluid, comprising inserting the tip and at least a part of the shank of the probe according to claim 1 into the fluid, flowing a solution from the inlet port through the channel and back to the outlet port while the probe is inserted, collecting a fraction or fractions of the solution as it emerges from the outlet port, and analyzing the collected fraction or fractions for the presence of the molecule.

17. The method according to claim 16, wherein the solution and the fluid are isotonic.

18. The method according to claim 16, wherein the porous layer is characterized by a pore density of $8\pm2\times10^{13}$ per square meter.

19. The method according to claim 16, wherein the porous layer is characterized by a porosity of 16 to 70 percent, where the porosity is defined as the ratio of the area of the pores to the area of the membrane.

20. A method for delivering molecules into a fluid, comprising inserting the tip and at least a part of the shank covered by the porous membrane of the probe according to claim 1 into the fluid, flowing a solution from the inlet port through the channel and back to the outlet port while the probe is inserted, wherein the solution has a higher concentration of the molecule than the fluid and the molecules pass by dialysis from the solution through the membrane into the fluid.

21. The method according to claim 20, wherein the solution and the fluid are isotonic.

22. The method according to claim 20, wherein the porous layer is characterized by a pore density of $8\pm2\times10^{13}$ per square meter.

23. The method according to claim 20, wherein the porous layer is characterized by a porosity of 16 to 70 percent, where the porosity is defined as the ratio of the area of the pores to the area of the membrane.

24. A method for forming a dialysis membrane over the single channel in the microfabricated microdialysis probe of claim 1, comprising:
  forming a polysilicon layer over the single channel;
  depositing a layer of aluminum over the polysilicon layer;
  anodizing the aluminum layer to make a layer of porous anodized aluminum oxide that is a mask on top of the underlying polysilicon layer;
  forming holes in the polysilicon layer by deep reactive ion etching through the porous anodized aluminum oxide mask to make the dialysis membrane covering the single channel.

25. The method of claim 24, wherein the single channel is formed at the surface of a silicon body.

26. The method of claim 24, further comprising removing the porous anodized aluminum oxide mask, depositing a fresh layer of aluminum, and anodizing the fresh aluminum layer to provide a fresh layer of porous anodized aluminum oxide.

27. The method of claim 26, wherein the fresh layer of aluminum and the fresh layer of porous anodized aluminum oxide has a thickness greater than the thickness of the porous anodized aluminum oxide mask.

* * * * *